United States Patent
Macpherson et al.

(10) Patent No.: US 11,531,445 B1
(45) Date of Patent: Dec. 20, 2022

(54) ANCESTRY PAINTING

(71) Applicant: 23andMe, Inc., Sunnyvale, CA (US)

(72) Inventors: John Michael Macpherson, Santa Ana, CA (US); Brian Thomas Naughton, Mountain View, CA (US); Joanna Louise Mountain, Menlo Park, CA (US)

(73) Assignee: 23andMe, Inc., Sunnyvale, CA (US)

( * ) Notice: Subject to any disclaimer, the term of this patent is extended or adjusted under 35 U.S.C. 154(b) by 0 days.

(21) Appl. No.: 17/682,761

(22) Filed: Feb. 28, 2022

Related U.S. Application Data

(63) Continuation of application No. 16/226,116, filed on Dec. 19, 2018, which is a continuation of application No. 15/267,053, filed on Sep. 15, 2016, now abandoned, which is a continuation of application No. 12/381,992, filed on Mar. 18, 2009, now abandoned.

(60) Provisional application No. 61/070,310, filed on Mar. 19, 2008.

(51) Int. Cl.
  *G06F 3/048* (2013.01)
  *G06F 3/04812* (2022.01)
  *G06F 3/0484* (2022.01)
  *G16B 20/40* (2019.01)

(52) U.S. Cl.
  CPC ........ *G06F 3/04812* (2013.01); *G06F 3/0484* (2013.01); *G16B 20/40* (2019.02)

(58) Field of Classification Search
  CPC .... G06F 3/04812; G06F 3/0484; G16B 20/40
  See application file for complete search history.

(56) References Cited

U.S. PATENT DOCUMENTS

| | | | |
|---|---|---|---|
| 5,692,501 | A | 12/1997 | Minturn |
| 6,570,567 | B1 | 5/2003 | Eaton |
| 6,703,228 | B1 | 3/2004 | Landers et al. |
| 7,142,205 | B2 | 11/2006 | Chithambaram et al. |
| 7,567,894 | B2 | 7/2009 | Durand et al. |
| 7,729,863 | B2 | 6/2010 | Ostrander et al. |
| 7,797,302 | B2 | 9/2010 | Kenedy et al. |

(Continued)

FOREIGN PATENT DOCUMENTS

| | | |
|---|---|---|
| WO | WO-2006089238 A2 | 8/2006 |
| WO | WO-2009002942 A2 | 12/2008 |

(Continued)

OTHER PUBLICATIONS

23andMeBlog [webpage] "New Feature: Ancestry Painting," by 23andMe, Ancestry, published online Mar. 25, 2008, pp. 1. [retrieved May 23, 2018] URL:https://blog.23andme.com/23andme-and-you/new-feature-ancestry-painting/.

(Continued)

*Primary Examiner* — Lisa S Landis
(74) *Attorney, Agent, or Firm* — McDonnell Boehnen Hulbert & Berghoff LLP; David K. Buckingham

(57) ABSTRACT

Displaying an indication of ancestral data is disclosed. An indication that a genetic interval corresponds to a reference interval that has a likelihood of having one or more ancestral origins is received. One or more graphic display parameters are determined based at least in part on the indication. An indication of the one or more ancestral origins is visually displayed using the one or more graphic display parameters.

17 Claims, 20 Drawing Sheets
(12 of 20 Drawing Sheet(s) Filed in Color)
Specification includes a Sequence Listing.

(56) References Cited

U.S. PATENT DOCUMENTS

| | | |
|---|---|---|
| 7,818,281 B2 | 10/2010 | Kennedy et al. |
| 7,818,310 B2 | 10/2010 | Kenedy et al. |
| 7,844,609 B2 | 11/2010 | Kenedy et al. |
| 7,848,914 B2 | 12/2010 | Durand et al. |
| 7,917,438 B2 | 3/2011 | Kenedy et al. |
| 7,933,912 B2 | 4/2011 | Kenedy et al. |
| 7,941,329 B2 | 5/2011 | Kenedy et al. |
| 7,941,434 B2 | 5/2011 | Kenedy et al. |
| 7,951,078 B2 | 5/2011 | Scheuner |
| 7,957,907 B2 | 6/2011 | Sorenson et al. |
| 7,983,893 B2 | 7/2011 | Durand et al. |
| 8,024,348 B2 | 9/2011 | Kenedy et al. |
| 8,051,033 B2 | 11/2011 | Kenedy et al. |
| 8,055,643 B2 | 11/2011 | Kenedy et al. |
| 8,065,324 B2 | 11/2011 | Kenedy et al. |
| 8,099,424 B2 | 1/2012 | Kenedy et al. |
| 8,108,406 B2 | 1/2012 | Kenedy et al. |
| 8,185,461 B2 | 5/2012 | Kenedy et al. |
| 8,187,811 B2 | 5/2012 | Eriksson et al. |
| 8,195,446 B2 | 6/2012 | Durand et al. |
| 8,200,509 B2 | 6/2012 | Kenedy et al. |
| 8,207,316 B1 | 6/2012 | Bentwich |
| 8,209,319 B2 | 6/2012 | Kenedy et al. |
| 8,214,192 B2 | 7/2012 | Durand et al. |
| 8,214,195 B2 | 7/2012 | Durand et al. |
| 8,224,835 B2 | 7/2012 | Kenedy et al. |
| 8,255,403 B2 | 8/2012 | Kenedy et al. |
| 8,285,486 B2 | 10/2012 | Martin et al. |
| 8,326,648 B2 | 12/2012 | Kenedy et al. |
| 8,386,519 B2 | 2/2013 | Kenedy et al. |
| 8,428,886 B2 | 4/2013 | Wong et al. |
| 8,443,339 B2 | 5/2013 | LeTourneau |
| 8,452,619 B2 | 5/2013 | Kenedy et al. |
| 8,458,097 B2 | 6/2013 | Kenedy et al. |
| 8,458,121 B2 | 6/2013 | Kenedy et al. |
| 8,463,554 B2 | 6/2013 | Hon et al. |
| 8,467,976 B2 | 6/2013 | Lo et al. |
| 8,473,273 B2 | 6/2013 | Durand et al. |
| 8,510,057 B1 | 8/2013 | Avey et al. |
| 8,543,339 B2 | 9/2013 | Wojcicki et al. |
| 8,589,437 B1 | 11/2013 | Khomenko et al. |
| 8,606,761 B2 | 12/2013 | Kenedy et al. |
| 8,645,118 B2 | 2/2014 | Durand et al. |
| 8,645,343 B2 | 2/2014 | Wong et al. |
| 8,655,899 B2 | 2/2014 | Kenedy et al. |
| 8,655,908 B2 | 2/2014 | Kenedy et al. |
| 8,655,915 B2 | 2/2014 | Kenedy et al. |
| 8,666,271 B2 | 3/2014 | Saiki |
| 8,666,721 B2 | 3/2014 | Durand et al. |
| 8,685,737 B2 | 4/2014 | Serber et al. |
| 8,719,045 B2 | 5/2014 | Yoon et al. |
| 8,731,819 B2 | 5/2014 | Dzubay et al. |
| 8,738,297 B2 | 5/2014 | Sorenson et al. |
| 8,786,603 B2 | 7/2014 | Rasmussen et al. |
| 8,788,283 B2 | 7/2014 | Kenedy et al. |
| 8,788,286 B2 | 7/2014 | Kenedy et al. |
| 8,798,915 B2 | 8/2014 | Dzubay et al. |
| 8,855,935 B2 | 10/2014 | Myres et al. |
| 8,990,250 B1 | 3/2015 | Chowdry et al. |
| 9,026,423 B2 | 5/2015 | Durand et al. |
| 9,031,870 B2 | 5/2015 | Kenedy et al. |
| 9,116,882 B1 | 8/2015 | Macpherson et al. |
| 9,170,992 B2 | 10/2015 | Kenedy et al. |
| 9,213,944 B1 | 12/2015 | Do et al. |
| 9,213,947 B1 | 12/2015 | Do et al. |
| 9,218,451 B2 | 12/2015 | Wong et al. |
| 9,262,567 B2 | 2/2016 | Durand et al. |
| 9,323,632 B2 | 4/2016 | Durand et al. |
| 9,336,177 B2 | 5/2016 | Hawthorne et al. |
| 9,367,663 B2 | 6/2016 | Deciu et al. |
| 9,367,800 B1 | 6/2016 | Do et al. |
| 9,390,225 B2 | 7/2016 | Barber et al. |
| 9,405,818 B2 | 8/2016 | Chowdry et al. |
| 9,582,647 B2 | 2/2017 | Kenedy et al. |
| 9,836,576 B1 | 12/2017 | Do et al. |
| 9,864,835 B2 | 1/2018 | Avey et al. |
| 9,886,576 B2 | 2/2018 | Urakabe |
| 9,977,708 B1 | 5/2018 | Do et al. |
| 10,025,877 B2 | 7/2018 | Macpherson |
| 10,162,880 B1 | 12/2018 | Chowdry et al. |
| 10,275,569 B2 | 4/2019 | Avey et al. |
| 10,296,847 B1 | 5/2019 | Do et al. |
| 10,379,812 B2 | 8/2019 | Kenedy et al. |
| 10,432,640 B1 | 10/2019 | Hawthorne et al. |
| 10,437,858 B2 | 10/2019 | Naughton et al. |
| 10,516,670 B2 | 12/2019 | Hawthorne et al. |
| 10,572,831 B1 | 2/2020 | Do et al. |
| 10,643,740 B2 | 5/2020 | Avey et al. |
| 10,658,071 B2 | 5/2020 | Do et al. |
| 10,691,725 B2 | 6/2020 | Naughton et al. |
| 10,699,803 B1 | 6/2020 | Do et al. |
| 10,755,805 B1 | 8/2020 | Do et al. |
| 10,777,302 B2 | 9/2020 | Chowdry et al. |
| 10,790,041 B2 | 9/2020 | Macpherson et al. |
| 10,803,134 B2 | 10/2020 | Kenedy et al. |
| 10,841,312 B2 | 11/2020 | Hawthorne et al. |
| 10,854,318 B2 | 12/2020 | Macpherson et al. |
| 10,891,317 B1 | 1/2021 | Chowdry et al. |
| 10,896,233 B2 | 1/2021 | Kenedy et al. |
| 10,936,626 B1 | 3/2021 | Naughton et al. |
| 10,957,455 B2 | 3/2021 | Kenedy et al. |
| 10,991,467 B2 | 4/2021 | Kenedy et al. |
| 10,999,285 B2 | 5/2021 | Hawthorne et al. |
| 11,003,694 B2 | 5/2021 | Kenedy et al. |
| 11,031,101 B2 | 6/2021 | Hon et al. |
| 11,049,589 B2 | 6/2021 | Hon et al. |
| 11,170,047 B2 | 11/2021 | Macpherson |
| 11,170,873 B2 | 11/2021 | Avey et al. |
| 11,171,962 B2 | 11/2021 | Hawthorne et al. |
| 11,322,227 B2 | 5/2022 | Hon et al. |
| 2002/0095585 A1 | 7/2002 | Scott |
| 2002/0133495 A1 | 9/2002 | Rienhoff, Jr. et al. |
| 2003/0113727 A1 | 6/2003 | Girn et al. |
| 2003/0113729 A1 | 6/2003 | DaQuino et al. |
| 2003/0135096 A1 | 7/2003 | Dodds |
| 2003/0172065 A1 | 9/2003 | Sorenson et al. |
| 2003/0179223 A1 | 9/2003 | Ying et al. |
| 2003/0186244 A1 | 10/2003 | Margus et al. |
| 2004/0002818 A1 | 1/2004 | Kulp et al. |
| 2004/0088191 A1 | 5/2004 | Holden |
| 2004/0175700 A1 | 9/2004 | Geesaman |
| 2004/0229213 A1 | 11/2004 | Legrain et al. |
| 2004/0229231 A1 | 11/2004 | Frudakis et al. |
| 2004/0241730 A1 | 12/2004 | Yakhini et al. |
| 2005/0039110 A1 | 2/2005 | De La Vega et al. |
| 2005/0191731 A1 | 9/2005 | Judson et al. |
| 2006/0003354 A1 | 1/2006 | Krantz et al. |
| 2006/0046256 A1 | 3/2006 | Halldorsson et al. |
| 2006/0100872 A1 | 5/2006 | Yokoi |
| 2006/0161460 A1 | 7/2006 | Smitherman et al. |
| 2006/0166224 A1 | 7/2006 | Norviel |
| 2006/0257888 A1 | 11/2006 | Zabeau et al. |
| 2007/0037182 A1 | 2/2007 | Gaskin et al. |
| 2007/0178500 A1 | 8/2007 | Martin et al. |
| 2007/0250809 A1 | 10/2007 | Kennedy et al. |
| 2007/0277267 A1 | 11/2007 | Byrum |
| 2008/0004848 A1 | 1/2008 | Avey |
| 2008/0081331 A1 | 4/2008 | Myres et al. |
| 2008/0131887 A1 | 6/2008 | Stephan et al. |
| 2008/0154566 A1 | 6/2008 | Myres et al. |
| 2008/0189047 A1 | 8/2008 | Wong et al. |
| 2008/0227063 A1 | 9/2008 | Kenedy et al. |
| 2008/0228043 A1 | 9/2008 | Kenedy et al. |
| 2008/0228410 A1 | 9/2008 | Kenedy et al. |
| 2008/0228451 A1 | 9/2008 | Kenedy et al. |
| 2008/0228677 A1 | 9/2008 | Kenedy et al. |
| 2008/0228698 A1 | 9/2008 | Kenedy et al. |
| 2008/0228699 A1 | 9/2008 | Kenedy et al. |
| 2008/0228700 A1 | 9/2008 | Kenedy et al. |
| 2008/0228701 A1 | 9/2008 | Kenedy et al. |
| 2008/0228702 A1 | 9/2008 | Kenedy et al. |
| 2008/0228704 A1 | 9/2008 | Kenedy et al. |
| 2008/0228705 A1 | 9/2008 | Kenedy et al. |
| 2008/0228706 A1 | 9/2008 | Kenedy et al. |

(56) References Cited

U.S. PATENT DOCUMENTS

| | | |
|---|---|---|
| 2008/0228708 A1 | 9/2008 | Kenedy et al. |
| 2008/0228722 A1 | 9/2008 | Kenedy et al. |
| 2008/0228753 A1 | 9/2008 | Kenedy et al. |
| 2008/0228756 A1 | 9/2008 | Kenedy et al. |
| 2008/0228757 A1 | 9/2008 | Kenedy et al. |
| 2008/0228765 A1 | 9/2008 | Kenedy et al. |
| 2008/0228766 A1 | 9/2008 | Kenedy et al. |
| 2008/0228767 A1 | 9/2008 | Kenedy et al. |
| 2008/0228768 A1 | 9/2008 | Kenedy et al. |
| 2008/0228797 A1 | 9/2008 | Kenedy et al. |
| 2008/0243843 A1 | 10/2008 | Kenedy et al. |
| 2008/0255768 A1 | 10/2008 | Martin et al. |
| 2008/0270366 A1 | 10/2008 | Frank |
| 2009/0043752 A1 | 2/2009 | Kenedy et al. |
| 2009/0099789 A1 | 4/2009 | Stephan et al. |
| 2009/0112871 A1 | 4/2009 | Hawthorne et al. |
| 2009/0118131 A1 | 5/2009 | Avey et al. |
| 2009/0119083 A1 | 5/2009 | Avey et al. |
| 2009/0182579 A1 | 7/2009 | Liu |
| 2009/0198519 A1 | 8/2009 | McNamar |
| 2009/0299645 A1 | 12/2009 | Colby et al. |
| 2010/0042438 A1 | 2/2010 | Moore et al. |
| 2010/0063830 A1 | 3/2010 | Kenedy et al. |
| 2010/0063835 A1 | 3/2010 | Kenedy et al. |
| 2010/0063865 A1 | 3/2010 | Kenedy et al. |
| 2010/0070292 A1 | 3/2010 | Kenedy et al. |
| 2010/0070455 A1 | 3/2010 | Halperin et al. |
| 2010/0076950 A1 | 3/2010 | Kenedy et al. |
| 2010/0076988 A1 | 3/2010 | Kenedy et al. |
| 2010/0145981 A1 | 6/2010 | Wojcicki et al. |
| 2010/0169262 A1 | 7/2010 | Kenedy et al. |
| 2010/0169313 A1 | 7/2010 | Kenedy et al. |
| 2010/0169338 A1 | 7/2010 | Kenedy et al. |
| 2010/0191513 A1 | 7/2010 | Listgarten et al. |
| 2010/0281401 A1 | 11/2010 | Tebbs et al. |
| 2011/0078168 A1 | 3/2011 | Kenedy et al. |
| 2011/0130337 A1 | 6/2011 | Eriksson et al. |
| 2011/0184656 A1 | 7/2011 | Kenedy et al. |
| 2011/0257889 A1 | 10/2011 | Klammer et al. |
| 2012/0270190 A1 | 10/2012 | Kenedy et al. |
| 2012/0270794 A1 | 10/2012 | Eriksson et al. |
| 2012/0301864 A1 | 11/2012 | Bagchi et al. |
| 2013/0085728 A1 | 4/2013 | Tang et al. |
| 2013/0149707 A1 | 6/2013 | Sorenson et al. |
| 2013/0345988 A1 | 12/2013 | Avey et al. |
| 2014/0006433 A1 | 1/2014 | Hon et al. |
| 2014/0045705 A1 | 2/2014 | Bustamante et al. |
| 2014/0067280 A1 | 3/2014 | Vockley et al. |
| 2014/0067355 A1 | 3/2014 | Noto et al. |
| 2015/0227610 A1 | 8/2015 | Chowdry et al. |
| 2015/0248473 A1 | 9/2015 | Kenedy et al. |
| 2015/0347566 A1 | 12/2015 | Kenedy et al. |
| 2016/0026755 A1 | 1/2016 | Byrnes et al. |
| 2016/0103950 A1 | 4/2016 | Myres et al. |
| 2016/0171155 A1 | 6/2016 | Do et al. |
| 2016/0277408 A1 | 9/2016 | Hawthorne et al. |
| 2016/0350479 A1 | 12/2016 | Han et al. |
| 2017/0011042 A1 | 1/2017 | Kermany et al. |
| 2017/0017752 A1 | 1/2017 | Noto et al. |
| 2017/0053089 A1 | 2/2017 | Kenedy et al. |
| 2017/0185719 A1 | 6/2017 | Kenedy et al. |
| 2017/0220738 A1 | 8/2017 | Barber et al. |
| 2017/0228498 A1 | 8/2017 | Hon et al. |
| 2017/0262577 A1 | 9/2017 | Ball et al. |
| 2017/0277827 A1 | 9/2017 | Granka et al. |
| 2017/0277828 A1 | 9/2017 | Avey et al. |
| 2017/0329866 A1 | 11/2017 | Macpherson |
| 2017/0329891 A1 | 11/2017 | Macpherson et al. |
| 2017/0329899 A1 | 11/2017 | Bryc et al. |
| 2017/0329901 A1 | 11/2017 | Chowdry et al. |
| 2017/0329902 A1 | 11/2017 | Bryc et al. |
| 2017/0329904 A1 | 11/2017 | Naughton et al. |
| 2017/0329915 A1 | 11/2017 | Kittredge et al. |
| 2017/0329924 A1 | 11/2017 | Macpherson et al. |
| 2017/0330358 A1* | 11/2017 | Macpherson .......... G16B 45/00 |
| 2018/0181710 A1 | 6/2018 | Avey et al. |
| 2018/0307778 A1 | 10/2018 | Macpherson |
| 2019/0012431 A1 | 1/2019 | Hon et al. |
| 2019/0034163 A1 | 1/2019 | Kenedy et al. |
| 2019/0114219 A1 | 4/2019 | Do et al. |
| 2019/0139623 A1 | 5/2019 | Bryc et al. |
| 2019/0206514 A1 | 7/2019 | Avey et al. |
| 2019/0267115 A1 | 8/2019 | Avey et al. |
| 2019/0281061 A1 | 9/2019 | Hawthorne et al. |
| 2019/0384777 A1 | 12/2019 | Naughton et al. |
| 2020/0137063 A1 | 4/2020 | Hawthorne et al. |
| 2020/0210143 A1 | 7/2020 | Kenedy et al. |
| 2020/0372974 A1 | 11/2020 | Chowdry et al. |
| 2021/0020266 A1 | 1/2021 | Freyman et al. |
| 2021/0043278 A1 | 2/2021 | Hon et al. |
| 2021/0043279 A1 | 2/2021 | Hon et al. |
| 2021/0043280 A1 | 2/2021 | Hon et al. |
| 2021/0043281 A1 | 2/2021 | Macpherson et al. |
| 2021/0058398 A1 | 2/2021 | Hawthorne et al. |
| 2021/0074385 A1 | 3/2021 | Hon et al. |
| 2021/0082167 A1 | 3/2021 | Jewett et al. |
| 2021/0166452 A1 | 6/2021 | Jewett et al. |
| 2021/0166823 A1 | 6/2021 | Kenedy et al. |
| 2021/0193257 A1 | 6/2021 | Freyman et al. |
| 2021/0209134 A1 | 7/2021 | Kenedy et al. |
| 2021/0225458 A1 | 7/2021 | Hon et al. |
| 2021/0233665 A1 | 7/2021 | Kenedy et al. |
| 2021/0243094 A1 | 8/2021 | Holness et al. |
| 2021/0250357 A1 | 8/2021 | Hawthorne et al. |
| 2021/0313013 A1 | 10/2021 | Hon et al. |
| 2021/0375392 A1 | 12/2021 | Polcari et al. |
| 2022/0044761 A1 | 2/2022 | O'Connell et al. |
| 2022/0051751 A1 | 2/2022 | Wilton et al. |
| 2022/0103560 A1 | 3/2022 | Hawthorne et al. |
| 2022/0115139 A1 | 4/2022 | Paradarami et al. |
| 2022/0139501 A1 | 5/2022 | Hon et al. |
| 2022/0157405 A1 | 5/2022 | Avey et al. |
| 2022/0198726 A1 | 6/2022 | Jewett et al. |
| 2022/0223233 A1 | 7/2022 | Bryc et al. |

FOREIGN PATENT DOCUMENTS

| | | |
|---|---|---|
| WO | WO-2009042975 A1 | 4/2009 |
| WO | WO-2016073953 A1 | 5/2016 |
| WO | WO-2022036178 A1 | 2/2022 |
| WO | WO-2022076909 A1 | 4/2022 |
| WO | WO-2022087478 A1 | 4/2022 |

OTHER PUBLICATIONS

Akbani, R. et al., "Applying Support Vector Machines to Imbalanced Datasets", In Machine Learning: ECML 2004; Boulicaut, J.-F., Esposito, F., Giannotti, F., Pedreschi, D., Eds.; Lecture Notes in Computer Science; Springer Berlin Heidelberg: Berlin, Heidelberg, 2004; vol. 3201, pp. 39-50.

Alexander, et al., "Fast model-based estimation of ancestry in unrelated individuals" Genome Research 19, (2009) pp. 1655-1664.

Assareh, A., et al., "Interaction Trees: Optimizing Ensembles of Decision Trees for Gene-Gene Interaction Detections," 2012 11th International Conference on Machine Learning and Applications, vol. 1, Dec. 2012, pp. 616-621. doi:10.1109/ICMLA.2012.114.

Bercovici, et al., "Ancestry inference in complex admixtures via variablelength Markov chain linkage models" In Proceedings of the 16th Annual Conference on Research in Computational Molecular Biology (RECOMB 2012), pp. 12-28.

Bettinger, B., [webpage] "AncestryDNA Launches New Ethnicity Estimate," The Genetic Genealogist (Internet Blog), published online Sep. 12, 2013, pp. 1-4. [retrieved May 23, 2018] URL:https://thegeneticgenealogist.com/2013/09/12/ancestrydna-launches-new-ethnicity-estimate/.

Bettinger, B., [webpage] "AncestryDNA Officially Launches," The Genetic Genealogist (Internet Blog), published online May 3, 2012, pp. 1-2. [retrieved May 23, 2018] URL:https://thegeneticgenealogist.com/2012/05/03/ancestrydna-officially-launches/.

Bettinger, B., [webpage] "The Monday Morning DNA Testing Company Review â€" AncestryByDNA, The Genetic Genealogist

(56) References Cited

OTHER PUBLICATIONS (Internet Blog), published Feb. 26, 2007, p. 1. [retrieved May 23, 2018] URL:https://thegeneticgenealogist.com/2007/02/26/the-monday-morning-dna-testing-company-review-%E2%80%93-ancestrybydna/.

Bohringer, S., et al., "A Software Package for Drawing Ideograms Automatically," Online J Bioinformatics, vol. 1, 2002, pp. 51-61.

Boser, et al., "A training algorithm for optimal margin classifiers" In Proceedings of the fifth annual workshop on computational learning theory, ACM, 1992, pp. 144-152.

Brion, M., et al., "Introduction of a Single Nucleodite Polymorphism—Based Major Y-Chromosome Haplogroup Typing Kit Suitable for Predicting the Geographical Origin of Male Lineages," Electrophoresis, vol. 26, 2005, pp. 4411-4420.

Brisbin, et al., "PCAdmix: principal components-based assignment of ancestry along each chromosome in individuals with admixed ancestry from two or more populations" Human Biology, vol. 84, No. 4 (2012) pp. 343-364.

Browning, et al., "Rapid and Accurate Haplotype Phasing and Missing-Data Inference for Whole-Genome Association Studies by Use of Localized Haplotype Clustering," The American Journal of Human Genetics, vol. 81, Nov. 2007, pp. 1084-1097.

Browning, S.R., et al., "Haplotype phasing: existing methods and new developments," Nature Reviews | Genetics, vol. 12, Oct. 2011, pp. 703-714. doi:10.1038/nrg3054 [URL: http://www.nature.com/reviews/genetics].

Bryc, et al., "The Genetic Ancestry of African Americans, Latinos, and European Americans across the United States," The American Journal of Human Genetics, vol. 96, Jan. 8, 2015, pp. 37-53.

Burroughs et al., "Analysis of Distributed Intrusion Detection Systems Using Bayesian Methods," Performance, Computing and Communications Conference, 2002, 21st IEEE International. IEEE, 2002, pp. 329-334.

Bycroft, et al., "The UK Biobank resource with deep phenotyping and genomic data" Nature, 562(7726), pp. 203-209, Oct. 2018. ISSN 1476-4687.

Byrne, J. et al., "The simulation life-cycle: supporting the data collection and representaion phase," Simulation Conference (WSC), 2014 Wincer, pp. 2738-2749.

Cann, et al., "A human genome diversity cell line panel" Science, 296(5566), Apr. 12, 2002, vol. 296 No. 5566, pp. 261-262. doi:I0.1126/science.296.5566.261.

Cao, et al., "Design of Reliable System Based on Dynamic Bayesian Networks and Genetic Algorithm," Reliability and Maintainability Symposium (RAMS), 2012 Proceedings—Annual. IEEE, 2012.

Cardena, et al., "Assessment of the Relationship between Self-Declared Ethnicity, Mitochondrial Haplogroups and Genomic Ancestry in Brazilian Individuals," PLoS ONE, vol. 8, No. 4, Apr. 24, 2013, pp. 1-6.

Cavalli-Sforza, L., "The Human Genome Diversity Project: past, present and future," Nature Reviews, Genetics, vol. 6, Apr. 2005, pp. 333-340.

Churchhouse, et al., "Multiway Admixture Deconvolution Using Phased or Unphased Ancestral Panels," Wiley Periodical, Inc., Genetic Epidemiology, 2012, pp. 1-12.

Crawford, et al., "Evidence for substantial fine-scale variation in recombination rates across the human genome," Nature Genetics, vol. 36, No. 7, Jul. 2004, pp. 700-706.

De Francesco, L., et al., "Efficient Genotype Elimination via Adaptive Allele Consolidation," IEEE/ACM Transactions on Computational Biology and Bioinformatics (TCBB), vol. 9, No. 4, Jul. 2012, pp. 1180-1189. doi:10.1109/TCBB.2012.46.

Dean, M., et al., "Polymorphic Admixture Typing in Human Ethnic Populations," American Journal of Human Genetics, vol. 55:4, 1994, pp. 788-808.

Delaneau, et al., "A Linear complexity phasing method for thousands of genomes," Nature Methods, vol. 9, No. 2, Feb. 2012, pp. 179-184.

Dempster, et al., "Maximum likelihood from incomplete data via the EM algorithm" Journal of the Royal Statistical Society, Series B, 39(1), 1977, pp. 1-38.

Diaz-Papkovich, et al., "UMAP reveals cryptic population structure and phenotype heterogeneity in large genomic cohorts" PLOS Genetics, 15(II):e1008432, Nov. 1, 2019, pp. 1-24.

Do et al., "A scalable pipeline for local ancestry inference using thousands of reference individuals (Abstract)," From Abstract/Session Information for Program No. 3386W; Session Title: Evolutionary and Population Genetics), ASHG, Aug. 2012.

DODECAD Project, [webpage] "Clusters Galore results, K = 73 for Dodecad Project members (up to DOD581)" Dodecad Ancestry Project (Internet Blog), published Mar. 31, 2011, pp. 1-11. [retrieved May 23, 2018] URL:http://dodecad.blogspot.com/2011/03/.

Dr. D., [webpage] "Population Finder Traces Deep Ancestry," Dr. D Digs up Ancestors (Internet Blog), DNA Testing, published online Apr. 9, 2011, p. 1. [retrieved May 23, 2018] URL:http://blog.ddowell.com/2011/04/population-finder-traces-deep-ancestry.html.

Druet, Tom, et al., "A Hidden Markov Model Combining Linkage and Linkage Disequilibrium Information for Haplotype Reconstruction and Quantitative Trait Locus Fine Mapping," Genetics vol. 184, No. 3, Jun. 1955, pp. 789-798.

Durand, et al., "A scalable pipeline for local ancestry inference using tens of thousands of reference haplotypes" 23andMe, Inc., Oct. 7, 2020, pp. 1-14.

Durand, et al., "Ancestry Composition: A Novel, Efficient Pipeline for Ancestry Deconvolution" 23andMe White paper, Oct. 17, 2014, pp. 1-16.

Falush, et al., "Inference of population structure using multilocus genotype data:linked loci and correlated allele frequencies" Genetics 164, (2003) pp. 1567-1587.

Feng et al., "Mining Multiple Temporal Patterns of Complex Dynamic Data Systems," Computational Intelligence and Data Mining, IEEE, 2009, 7 pages.

Fuchsberger, et al., "Minimac2: faster genotype imputation," Bioinformatics, vol. 31, No. 5, Oct. 22, 2014, pp. 782-784. doi:10.1093/bioinformatics/btu704.

Goldberg, et al., "Autosomal Admixture Levels are Informative About Sex Bias in Admixed Populations," Genetics, Nov. 2014, vol. 198, pp. 1209-1229.

Gravel, S., "Population Genetics Models of Local Ancestry," Genetics, Jun. 2012, 191(2), pp. 607-619.

Green, et al., "A Draft Sequence of the Neandertal Genome," Science, Author Manuscript, available online in PMC Nov. 8, 2016, pp. 1-36.

Green, et al., "A Draft Sequence of the Neandertal Genome," Science, vol. 328, May 7, 2010, pp. 710-722.

Gu et al., "Phenotypic Selection for Dormancy Introduced a Set of Adaptive Haplotypes from Weedy Into Cultivated Rice," Genetics Society of America, vol. 171, Oct. 2005, pp. 695-704.

Gusev, et al., "Whole population, genome-wide mapping of hidden relatedness," Genome Research, vol. 19, 2009, pp. 318-326.

Halder, Indrani, et al., "A Panel of Ancestry Informative Markers for Estimating Individual Biogeographical Ancestry and Admixture From Four Continents: Utility and Applications," Human Mutation, vol. 29, No. 5, 2007, pp. 648-658.

He, D. et al., "IPEDX: An Exact Algorithm for Pedigree Reconstruction Using Genotype Data," 2013 IEEE International Conference on Bioinformatics and Biomedicine, 2013, pp. 517-520. doi: 10.1109/BIBM.2013.6732549.

He, et al., "Multiple Linear Regression for Index SNP Selection on Unphased Genotypes," Engineering in Medicine and Biology Society, EMBS Annual International Conference of the IEEE, Aug. 30-Sep. 3, 2006, pp. 5759-5762.

Hellenthal, et al. "A Genetic Atlas of Human Admixture History," Science, vol. 343, Feb. 14, 2014, pp. 747-751.

Henn, et al., "Cryptic Distant Relatives Are Common in Both Isolated and Cosmopolitan Genetic Samples" PLOS One, 7(4):e34267, Apr. 2012, pp. 1-13.

Hill, et al. "Identification of Pedigree Relationship from Genome Sharing," G3: Gene | Genomes | Genetics, vol. 3, Sep. 2013, pp. 1553-1571.

(56) References Cited

OTHER PUBLICATIONS

Howie, et al., "A Flexible and Accurate Genotype Imputation Method for the Next Generation of Genome-Wide Association Studies," PLoS Genetics, vol. 5, No. 6, Jun. 2009, pp. 1-15.
Howie, et al., "Fast and accurate genotype imputation in genome-wide association studies through pre-phasing," Nature Genetics, vol. 44, No. 8, Aug. 2012, pp. 955-960.
Huff, C.D., et al., (2011) "Maximum-likelihood estimation of recent shared ancestry (ERSA)" Genome Research, 21, pp. 768-774.
International Search Report and Written Opinion dated Dec. 29, 2020 issued in Application No. PCT/US2020/042628.
International Search Report and Written Opinion dated Nov. 15, 2021, in PCT Application No. PCT/US2021/045880.
International Search Report and Written Opinion dated Nov. 15, 2021 issued in Application No. PCT/US21/45880.
Jaakkola, et al., "Exploiting generative models in discriminative classifiers" Advances in neural information processing systems, (1999) pp. 487-493.
Jia, Jing et al. "Developing a novel panel of genome-wide ancestry informative markers for biogeographical ancestry estimates," Forensic Science International: Genetics, vol. 8 (2014) pp. 187-194.
Karakuzu, A., et al., "Assessment of In-Vivo Skeletal Muscle Mechanics During Joint Motion Using Multimodal Magnetic Resonance Imaging Based Approaches," Biomedical Engineering Meeting (BIYOMUT), 2014 18th National, pp. 1-4.
Kennedy, et al., "Visual Cleaning of Genotype Data," 2013 IEEE Symposium on Biological Data Visualization (BioVis), Atlanta, Ga., Oct. 2013, pp. 105-112. doi: 10.1109/BioVis.2013.6664353.
Kerchner, [webpage] "DNAPrint Test Results—East Asian vs Native American Minority Admixture Detection," PA Deutsch Ethnic Group DNA Project, created Jun. 26, 2004, updated May 27, 2005, pp. 1-9. [retrieved May 23, 2018] URL:http://www.kerchner.com/dnaprinteavsna.htm.
Kidd, et al. "Population Genetic Inference from Personal Genome Data: Impact of Ancestry and Admixture on Human Genomic Variation," The American Journal of Human Genetics, vol. 91, Oct. 5, 2012, pp. 660-671.
Kirkpatrick, B., et al. "Perfect Phylogeny Problems with Missing Values," IEEE/ACM Transactions on Computational Biology and Bioinformatics (TCBB), vol. 11, No. 5, Sep./Oct. 2014, pp. 928-941. doi:10.1109/TCBB.2014.2316005.
Kraak, M-J, "Visualising Spatial Distributions," Geographical Information Systems: Principles, Techniques, Applications and Management, New York, John Wiley and Sons, 1999, pp. 157-173.
Kumar, et al., "XGMix: Local-Ancestry Inference with Stacked XGBoost" bioRxiv, Apr. 21, 2020, 053876, pp. 1-8.
Lafferty, et al., "Conditional random fields: Probabilistic models for segmenting and labeling sequence data" Proceedings of the 18th International Conference on Machine Learning (ICML-2001), Jun. 28, 2001, pp. 1-10.
Lawson, et al., "Inference of Population Structure using Dense Haplotype Data," PLoS Genetics, vol. 8, No. 1, Jan. 2012, pp. 1-16.
Lazaridis et al., "Ancient Human Genomes Suggest Three Ancestral Populations for Present-Day Europeans," Nature, Author Manuscript available online in PMC Mar. 1, 20158, pp. 1-33.
Lazaridis et al., "Ancient Human Genomes Suggest Three Ancestral Populations for Present-Day Europeans," Nature, vol. 513, Sep. 18, 2014, doi:10.1038/nature 13673, pp. 409-413.
Lee, et al., "Comparing genetic ancestry and self-reported race/ethnicity in a multiethnic population in New York City," Journal of Genetics, vol. 89, No. 4, Dec. 2010, pp. 417-423.
Lei, X. et al., "Cloud-Assisted Privacy-Preserving Genetic Paternity Test," 2015 IEEE/CIC International Conference on Communications in China (ICCC), Apr. 7, 2016, pp. 1-6. doi: 10.1109/ICCChina.2015.7448655.
Li, et al., "Modeling linkage disequilibrium and identifying recombination hotspots using single-nucleotide polymorphism data" Genetics 165, (2003) pp. 2213-2233.
Li, et al. "Worldwide Human Relationships Inferred from Genome-Wide Patterns of Variation," Science, vol. 319, Feb. 22, 2008, pp. 1100-1104.
Li, X., et al., "Integrating Phenotype-Genotype Data for Prioritization of Candidate Symptom Genes," 2013 IEEE International Conference on Bioinformatics and Biomedicine, Dec. 2013, pp. 279-280. doi: 10.1109/BIBM.2013.6732693.
Liang et al., "A Deterministic Sequential Monte Carlo Method for Haplotype Inference," IEEE Journal of Selected Topics in Signal Processing, vol. 2, No. 3, Jun. 2008, pp. 322-331.
Liang et al., "The Lengths of Admixture Tracts," Genetics, vol. 197, Jul. 2014, pp. 953-967. doi:10.1534/genetics.114.162362.
Lin et al. "Polyphase Speech Recognition," Acoustics, Speech and Signal Processing, IEEE International Conference on 2008, IEEE, 2008, 4 pages.
Lipson, et al., "Reconstructing Austronesian population history in Island Southeast Asia," Nature Communications, 5:4689, DOI: 10.1038/ncomms5689, 2014, pp. 1-7.
Li, H., et al., "Relationship Estimation from Whole-Genome Sequence Data" PLoS Genet 10(1); (2014) e1004144. doi:10.1371liournal.pgen.1004144.
Loh, et al., "Inferring Admixture Histories of Human Populations Using Linkage Disequilibrium," Genetics, 193(4), Apr. 2013, pp. 1233-1254.
Loh, et al., "Reference-based phasing using the Haplotype Reference Consortium panel" Nat. Genet. Nov. 2016; 48(11): pp. 1443-1448. doi:I0.1038/ng.3679.
Mahieu, L., [webpage] "My (free) Ancestry.com DNA results—a comparison to FamilyTreeDNA," Genejourneys (Internet Blog), published online Mar. 6, 2012, pp. 1-3. [retrieved May 23, 2018] URL:https://genejourneys.com/2012/03/06/my-free-ancestry-com-dna-results-a-comparison-to-familytreedna/.
Maples, et al. "RFMix: A Discriminitve Modeling Approach for Rapid and Robust Local-Ancestry Inference," American Journal of Human Genetics (AJHG) vol. 93, No. 2, Aug. 8, 2013, pp. 278-288. [retreived Nov. 12, 2015] URL: https://doi.org/10.1016/j.ajhg.2013.06.020.
McCarthy, et al., "A reference panel of 64,976 haplotypes for genotype imputation" Nature genetics, 48(10), Oct. 2016, pp. 1279-1283.
Mcinnes, et al., "UMAP: Uniform Manifold Approximation and Projection for Dimension Reduction" arXiv preprint arXiv: 1802.03426 (2018), pp. 1-63.
Mersha, Tesfaye et al. "Self-reported race/ethnicity in the age of genomic research: its potential impact on understanding health disparities," Human Genomics, vol. 9, No. 1 (2015) pp. 1-15.
Montinaro, Francesco et al. "Unraveling the hidden ancestry of American admixed populations," Nature Communications, Mar. 24, 2015, pp. 1-7. doi:10.1038/ncomms7596.
Montserrat, et al., "LAI-Net: Local-ancestry inference with neural networks" ICASSP 2020-2020 IEEE International Conference on Acoustics, Speech and Signal Processing (ICASSP), May 2020, pp. 1314-1318.
Moore, C., [webpage] "LivingSocial's AncestrybyDNA Offer is Not the AncestryDNA Test!" Your Genetic Genealogist (Internet Blog), published online Sep. 18, 2012, pp. 1-2. [retrieved May 23, 2018] URL:http://www.yourgeneticgenealogist.com/2012/09/livingsocials-ancestrybydna-offer-is.html.
Moore, C., [webpage] "New Information on Ancestry.com's AncestryDNA Product," Your Genetic Geneologist (Internet Blog), published online Mar. 30, 2012, pp. 1-3. [retrieved May 23, 2018] URL:http://www.yourgeneticgenealogist.com/2012/03/new-information-on-ancestrycoms.html.
Moreno-Estrada, et al., "Reconstructing the Population Genetic History of the Caribbean," PLoS Genetics, 9(11), e1003925, Nov. 14, 2013, pp. 1-19.
Ng, et al., "On discriminative vs. generative classifiers: A comparison of logistic regression and nai:ve Bayes" Advances in neural information processing systems, 14:841, 2002.
Nievergeit, Caroline, et al., "Inference of human continental origin and admixture proportions using a highly discriminative ancestry informative 41-SNP panel," Investigative Genetics, vol. 4, No. 13(2013), pp. 1-16.

(56) References Cited

OTHER PUBLICATIONS

Novembre, et al., "Perspectives on human population structure at the cusp of the sequencing era" Annual Review of Genomics and Human Genetics, 12(1); 2011, pp. 245-274.
Novembre, et al. "Recent advances in the study of fine-scale population structure in humans," Current Opinion in Genetics & Development, vol. 41 (2016), pp. 98-105. URL:http://dx.doi.org/10.1016/.
O'Dushlaine, C. et al. "Genes Predict Village of Origin in Rural Europe", European Journal of Human Genetics 2010, vol. 18, No. 11, pp. 1269-1270.
Omberg, L., et al., "Inferring Genome-Wide Patterns of Admixture in Qataris Using Fifty-Five Ancestral Populations," BMC Genetics, 2012, ISSN 1471-2156, BioMed Central, Ltd., 18 pages.
Pasaniuc et al., "Highly Scalable Genotype Phasing By Entropy Minimization," Engineering in Medicine and Biology Society, 2006, EMBS'06, 28th Annual International Conference of the IEEE, 2006, 5 pages.
Pasaniuc, et al., "Inference of locus-specific ancestry in closely related populations," Bioinformatics, 25(12) Jun. 2009, pp. i213-i221.
Patterson, et al., "Methods for High-Density Admixture Mapping of Disease Genes," AJHG, vol. 74, No. 5, May 2004, pp. 1-33.
Patterson, et al., "Population Structure and Eigenanalysis," PLoS Genetics, vol. 2, No. 12, e190, Dec. 2006, pp. 2074-2093.
Phelps, C.I., et al. "Signal Classification by probablistic reasoning," Radio and Wireless Symposium (RWS), 2013 IEEE Year: 2013, pp. 154-156.
Phillips, et al., "Inferring Ancestral Origin Using a Single Multiplex Assay of Ancestry-Informative Marker SNPs," Forensic Science International, Genetics, vol. 1, 2007, pp. 273-280.
Pirola, et al., "A Fast and Practical Approach to Genotype Phasing and Imputation on a Pedigree with Erroneous and Incomplete Information," IEEE/ACM Transactions on Computational Biology and Bioinformatics, vol. 9, No. 6. Nov./Dec. 2012, pp. 1582-1594.
Pool, et al., "Inference of Historical Changes in Migration Rate From the Lengths of Migrant Tracts," Genetics, 181(2), Feb. 2009, pp. 711-719.
Porras-Hurtado, et al., "An overview of STRUCTURE: applications, parameter settings, and supporting software," Frontiers in Genetics, vol. 4, No. 96, May 29, 2013, pp. 1-13.
Price, et al. "Sensitive Detection of Chromosomal Segments of Distinct Ancestry in Admixed Populations," PLoS Genetics, vol. 5, No. 6, Jun. 19, 2009 (e1000519) pp. 1-18.
Price, et al., "New approaches to population stratification in genome-wide association studies" Nature Reviews Genetics, 11(7): Jun. 2010, pp. 459-463.
Pritchard, et al., "Association Mapping in Structured Populations," Am. J. Hum. Genet., vol. 67, 2000, pp. 170-181.
Pritchard, et al., "Inference of population structure using multilocus genotype data" Genetics 155, (2000) pp. 945-959.
Purcell, et al., "PLINK: A Tool Set for Whole-Genome Association and Population-Based Linkage Analysis," The American Journal of Human Genetics, vol. 81, Sep. 2007, pp. 559-575.
Rabiner, L., "A Tutorial on Hidden Markov Models and Selected Applications in Speech Recognition," Proceedings of the IEEE, vol. 77, No. 2, Feb. 1989, pp. 257-286.
Ratsch, et al., "Learning Interpretable SVMs for Biological Sequence Classification" BMC Bioinformatics, Mar. 20, 2006, 7(Suppl1):S9, pp. 1-14.
Reddit.com [Webpage] "Potential Incoming Algorithm Update (Ancestry Composition v5.9)_23andme" posted by u/Spacemutantl4 (Aug. 12, 2020) pp. 1-7. URL:https://www.reddit.com/r/23andme/comments/i7pggm/potential_incoming_algorithm_update_ancestry/.
Royal, et al. "Inferring Genetic Ancestry: Opportunities, Challenges, and Implications," The American Journal of Human Genetics, vol. 86, May 14, 2010, pp. 661-673.
Sampson, et al., "Selecting SNPs to Identify Ancestry" Ann. Hum. Genet. 2011, 75(4) Jul. 2011, pp. 539-553.
Sankararaman, et al., "Estimating Local Ancestry in Admixed Populations," The American Journal of Human Genetics, vol. 82, Feb. 2008, pp. 290-303.
Sankararaman, et al., "On the inference of ancestries in admixed populations," Genome Research, Mar. 2008, vol. 18, pp. 668-675.
Scheet, et al., "A Fast and Flexible Statistical Model for Large-Scale Population Genotype Data: Applications to Inferring Missing Genotypes and Haplotypic Phase," The American Journal of Human Genetics, vol. 78, Apr. 2006, pp. 629-644.
Seldin, et al., "New approaches to disease mapping in admixed populations" Nature Reviews Genetics, 12(8): Aug. 2011, pp. 523-528. doi: 10.1038/nrg3002.
Sengupta, et al., "Polarity and Temporality of High-Resolution Y-Chromosome Distributions in India Identify Both Indigenous and Exogenous Expansions and Reveal Minor Genetic Influence of Central Asian Pastoralists," The American Journal of Human Genetics, vol. 78, Feb. 2006, pp. 202-221.
Shriver, et al., "Ethnic-Affiliation Estimation by Use of Population-Specific DNA Markers," American Journal of Human Genetics, vol. 60, 1997, pp. 957-964.
Shriver, et al., "Genetic ancestry and the Search for Personalized Genetic Histories," Nature Reviews Genetics, vol. 5, Aug. 2004, pp. 611-618.
Shriver, M.D et al., "The Genomic Distribution of Population Substructure in Four Populations Using 8,525 Autosomal SNPs", Human Genomics, 2004, vol. 1, No. 4, pp. 274-286.
Sohn, et al. "Robust Estimation of Local Genetic Ancestry in Admixed Populations Using a Nonparametric Bayesian Approach," Genetics, vol. 191, Aug. 2012, pp. 1295-1308.
Stephens, et al., "A Comparison of Bayesian Methods for Haplotype Reconstruction from Population Genotype Data," Am. J. Hum. Genet., vol. 73, 2003, pp. 1162-1169.
Stephens, et al., "A New Statistical Method for Haplotype Reconstruction from Population Data," Am. J. Hum. Genet., vol. 68, 2001, pp. 978-989.
Stephens, et al., "Accounting for Decay of Linkage Disequilibrium in Haplotype Inference and Missing-Data Imputation," Am. J. Hum. Genet., vol. 76, 2005, pp. 449-462.
Sundquist, et al., "Effect of genetic divergence in identifying ancestral origin using HAPAA" Genome Research, vol. 18, No. 4, Apr. 2008, pp. 676-682.
Tang, et al., "Estimation of individual admixture: Analytical and study design considerations" Genet. Epidem. 28, (2005) pp. 289-301.
Tang, et al., "Reconstructing Genetic Ancestry Blocks in Admixed Individuals," The American Journal of Human Genetics, vol. 79, No. 1, Jul. 2006, pp. 1-12.
The 1000 Genomes Project Consortium "A global reference for human genetic variation" Nature, 526(7571); 2015, pp. 68-74. ISSN 1476-4687.
The International HapMap Consortium, "A haplotype map of the human genome" vol. 437, Oct. 27, 2005, pp. 1299-1320. doi:10.1038/nature04226.
The International HapMap Consortium, "A second generation human haplotype map of over 3.1 million SNPs," Nature, vol. 449, Oct. 18, 2007, pp. 851-860. doi:10.1038/nature06258.
Thiele, H., et al., HaploPainter: a tool for drawing Pedigrees with complex haplotypes, vol. 21 No. 8, 2005, pp. 1730-1732.
Thornton, et al., "Local and Global Ancestry Inference, and Applications to Genetic Association Analysis for Admixed Populations" Genet. Epidemiol., Sep. 2014, 38(01): S5-S12. doi:10.1002/gepi.21819.
Uddin, et al., "Variability of Haplotype Phase and Its Effect on Genetic Analysis," Electrical and Computer Engineering, 2008, CCECE 2008, Canadian Conference on, IEEE, 2008, pp. 000596-000600.
Underhill, et al., "Use of Y Chromosome and Mitochondrial DNA Population Structure in Tracing Human Migrations," Annu. Rev. Genet., vol. 41, 2007, pp. 539-564.
U.S. Final Office Action dated Feb. 10, 2021, issued in U.S. Appl. No. 16/915,868.
U.S. Appl. No. 12/381,992, Macpherson et al., filed Mar. 18, 2009.
U.S. Appl. No. 16/219,597, Bryc et al., filed Dec. 13, 2018.

(56) References Cited

OTHER PUBLICATIONS

U.S. Appl. No. 16/226,116, Macpherson et al., filed Dec. 19, 2018.
U.S. Appl. No. 16/282,221, Do et al., filed Feb. 21, 2019.
U.S. Appl. No. 16/915,868, Do et al., filed Jun. 29, 2020.
U.S. Appl. No. 16/946,829, Bryc et al., filed Jul. 8, 2020.
U.S. Appl. No. 17/161,140, Do et al., filed Jan. 28, 2020.
U.S. Final Office Action dated Dec. 20, 2011, issued in U.S. Appl. No. 12/381,992.
U.S. Final Office Action dated Dec. 22, 2014, issued in U.S. Appl. No. 12/381,992.
U.S. Final Office Action dated Dec. 27, 2013, issued in U.S. Appl. No. 12/381,992.
U.S. Final Office Action dated Dec. 29, 2021 issued in U.S. Appl. No. 17/249,520.
U.S. Final Office Action dated Feb. 2, 2021, issued in U.S. Appl. No. 16/844,758.
U.S. Final Office Action dated Jan. 11, 2016 issued in U.S. Appl. No. 13/801,386.
U.S. Final Office Action dated Jan. 8, 2020 issued in U.S. Appl. No. 14/924,562.
U.S. Final Office Action dated Jun. 29, 2021 issued in U.S. Appl. No. 15/950,023.
U.S. Final Office Action dated May 31, 2016 issued in U.S. Appl. No. 13/801,653.
U.S. Final Office Action dated Nov. 1, 2021 issued in U.S. Appl. No. 16/226,116.
U.S. Final Office Action dated Nov. 29, 2021 issued in U.S. Appl. No. 16/240,641.
U.S. Final Office Action dated Nov. 3, 2015, issued in U.S. Appl. No. 12/381,992.
U.S. Final Office action dated Oct. 1, 2021, in U.S. Appl. No. 17/161,140.
U.S. Final Office Action dated Sep. 13, 2018 issued in U.S. Appl. No. 14/924,562.
U.S. Final Office Action dated Sep. 4, 2018 issued in U.S. Appl. No. 14/924,552.
U.S. Non Final Office Action dated Feb. 4, 2022 in U.S. Appl. No. 16/282,221.
U.S. Non Final Office Action dated Jan. 24, 2022, in U.S. Appl. No. 17/387,940.
U.S. Non Final Office Action dated Jan. 5, 2022, in U.S. Appl. No. 15/950,023.
U.S. Non-Final Office action dated Oct. 1, 2021, in U.S. Appl. No. 16/844,758.
U.S. Notice of Allowance dated Apr. 2, 2020, issued in U.S. Appl. No. 16/446,465.
U.S. Notice of Allowance dated Apr. 29, 2019 issued in U.S. Appl. No. 14/938,111.
U.S. Notice of Allowance dated Aug. 12, 2015 issued in U.S. Appl. No. 13/801,056.
U.S. Notice of Allowance dated Aug. 12, 2015 issued in U.S. Appl. No. 13/801,552.
U.S. Notice of Allowance dated Aug. 14, 2018 issued in U.S. Appl. No. 15/181,083.
U.S. Notice of Allowance dated Dec. 28, 2017 issued in U.S. Appl. No. 13/801,653.
U.S. Notice of Allowance dated Feb. 26, 2020 issued in U.S. Appl. No. 15/181,088.
U.S. Notice of Allowance dated Feb. 4, 2015 issued in U.S. Appl. No. 13/801,552.
U.S. Notice of Allowance dated Jan. 20, 2016 issued in U.S. Appl. No. 13/800,683.
U.S. Notice of Allowance dated Jan. 9, 2020 issued in U.S. Appl. No. 14/938,111.
U.S. Notice of Allowance dated Jul. 24, 2017 issued in U.S. Appl. No. 13/801,386.
U.S. Notice of Allowance dated Jun. 26, 2015 issued in U.S. Appl. No. 13/801,552.
U.S. Notice of Allowance dated May 18, 2015 issued in U.S. Appl. No. 13/801,056.
U.S. Notice of Allowance dated May 3, 2016 issued in U.S. Appl. No. 13/800,683.
U.S. Notice of Allowance dated Nov. 12, 2019, issued in U.S. Appl. No. 16/044,364.
U.S. Notice of Allowance dated Nov. 15, 2018 issued in U.S. Appl. No. 15/181,083.
U.S. Office Action dated Apr. 19, 2017 issued in U.S. Appl. No. 13/801,653.
U.S. Office Action dated Aug. 12, 2015 issued in U.S. Appl. No. 13/800,683.
U.S. Office Action dated, Aug. 2, 2011, issued in U.S. Appl. No. 12/381,992.
U.S. Office Action dated Aug. 6, 2013, issued in U.S. Appl. No. 12/381,992.
U.S. Office Action dated Aug. 7, 2014, issued in U.S. Appl. No. 12/381,992.
U.S. Office Action dated Dec. 30, 2020 issued in U.S. Appl. No. 15/950,023.
U.S. Office Action dated Feb. 11, 2019, issued in U.S. Appl. No. 16/044,364.
U.S. Office Action dated Feb. 9, 2018 issued in U.S. Appl. No. 14/924,552.
U.S. Office Action dated Jan. 23, 2018 issued in U.S. Appl. No. 15/181,083.
U.S. Office Action dated Jan. 29, 2015 issued in U.S. Appl. No. 13/801,056.
U.S. Office Action dated Jan. 30, 2018 issued in U.S. Appl. No. 14/924,562.
U.S. Office Action dated Jul. 8, 2015 issued in U.S. Appl. No. 13/801,386.
U.S. Office Action dated Jun. 1, 2021 issued in U.S. Appl. No. 17/249,520.
U.S. Office Action dated Jun. 24, 2019 issued in U.S. Appl. No. 14/938,111.
U.S. Office Action dated Jun. 25, 2019 issued in U.S. Appl. No. 15/181,088.
U.S. Office Action dated Jun. 3, 2021, issued in U.S. Appl. No. 17/161,140.
U.S. Office Action dated Jun. 5, 2019 issued in U.S. Appl. No. 14/924,562.
U.S. Office Action dated Mar. 16, 2015 issued in U.S. Appl. No. 13/801,552.
U.S. Office Action dated Mar. 16, 2016, issued in U.S. Appl. No. 12/381,992.
U.S. Office Action dated May 22, 2015, issued in U.S. Appl. No. 12/381,992.
U.S. Office Action dated Oct. 11, 2019, issued in U.S. Appl. No. 16/446,465.
U.S. Office Action dated Oct. 20, 2020, issued in U.S. Appl. No. 16/915,868.
U.S. Office Action dated Oct. 27, 2016, issued in U.S. Appl. No. 13/801,386.
U.S. Office Action dated Oct. 5, 2020, issued in U.S. Appl. No. 16/844,758.
U.S. Office Action dated Sep. 25, 2018 issued in U.S. Appl. No. 14/938,111.
U.S. Office Action dated Sep. 26, 2018 issued in U.S. Appl. No. 15/267,053.
U.S. Office Action dated Sep. 30, 2015 issued in U.S. Appl. No. 13/801,653.
U.S. Appl. No. 17/387,940, filed Jul. 28, 2021, inventors Do, et al.
U.S. Appl. No. 17/443,946, filed Jul. 28, 2021, inventors Do, et al.
U.S. Appl. No. 17/444,989, filed Aug. 12, 2021, inventors Wilton, et al.
Vanitha, et al., "Implementation of an Integrated FPGA Based Automatic Test Equipment and Test Generation for Digital Circuits," Information Communication and Embedded Systems (ICICES), 2013 International Conference on. IEEE, 2013.
Ward, J.J. et al., "Secondary Structure Prediction with Support Vector Machines", Bioinformatics, 2003, vol. 19, No. 13, pp. 1650-1655.
Yang, et al., "Examination of Ancestry and Ethnic Affiliation Using Highly Informative Diallelic DNA Markers: Application to Diverse

(56) References Cited

OTHER PUBLICATIONS and Admixed Populations and Implications for Clinical Epidemiology and Forensic Medicine," Human Genetics, vol. 118, 2005, pp. 382-392.

Yoon, Byung-Jun, "Hidden Markov Models and their Applications in Biological Sequence Analysis," Current Genomics, vol. 10, 2009, pp. 402-415.

Yousef, Malik, et al., "Recursive Cluster Elimination (RCE) for Classification and Feature Selection From Gene Expression Data," BMC Bioinformatics, vol. 8, May 2007, pp. 1-12.

Yu, Haiyuan et al., "Total Ancestry Measure: quantifying the similarity in tree-like classification, with genomic applications" Bioinformatics, vol. 23, No. 16, May 31, 2007, pp. 2163-2173.

Zhou, Nina, et al., "Effective Selection of Informative SNPs and Classification on the HapMap Genotype Data," BMC Bioinformatics, vol. 8, No. 1, 2007, pp. 1-9.

Baran, Y. et al., "Fast and accurate inference of local ancestry in Latino populations", Bioinformatics, 2012, vol. 28, Issue 10, pp. 1359-1367.

U.S. Appl. No. 16/844,758, Do et al., filed Apr. 9, 2020.

U.S. Final Office action dated Apr. 11, 2022 in U.S. Appl. No. 16/844,758.

U.S. Non-Final Office Action dated Apr. 15, 2022 in U.S. Appl. No. 17/161,140.

U.S. Appl. No. 17/662,040, filed May 4, 2022.

U.S. Appl. No. 17/707,790, filed Mar. 29, 2022.

U.S. Final office Action dated Aug. 12, 2022 in U.S. Appl. No. 15/950,023.

U.S. Notice of Allowance dated Aug. 23, 2022 in U.S. Appl. No. 17/161,140.

\* cited by examiner

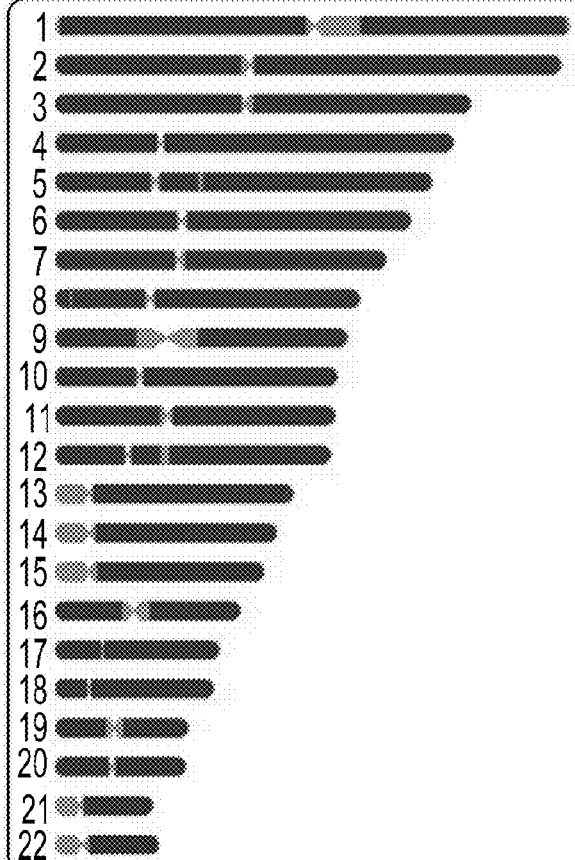
FIG. 1

200

SEQUENCE LISTING

```
<160> NUMBER OF SEQ ID NOS: 1

<210> SEQ ID NO 1
<211> LENGTH: 21
<212> TYPE: DNA
<213> ORGANISM: Homo sapiens

<400> SEQUENCE: 1
acaagtacct tgaaaaaatt t                                              21
```

Ancestry Painting

Trace the ancestry of your chromosomes, one segment at a time.

Chromosome View

- Solid segments indicate that both chromosomes come from the same geographic region. See a Cambodian Woman's painting.
- Dual-colored segments indicate chromosomes from different geographic regions. See an African American Man's painting.

Select a person: Greg Mendel (Dad) ⌄ — 202

Dropdown:
- Greg Mendel (Dad)
- Lilly Mendel (Mom)
- Erin Mendel (Daughter)
- Alan Mendel (Son)
- Ian Mendel (Son)
- Margo Fisher (Grandma)
- Ron Fisher (Grandpa)
- Fred Mendel (Grandpa)
- African American Man
- African American Woman
- Berber Woman
- Cambodian Woman
- Italian Man
- Indian Man
- Native American Woman
- Senegalese Man
- Uyghur Woman
- Chinese Person
- Japanese Person
- Nigerian Person Greg Mendel (Dad) 

- Europe 100%
- Asia 0%
- Africa 0%
- Not Genotyped

Worldwide Examples

Click on the icons in the map below to see example paintings of individuals from across the globe.

Ancestry Painting

Trace the ancestry of your chromosomes, one segment at a time.

Chromosome View

- Solid segments indicate that both chromosomes come from the same geographic region. See a Cambodian Woman's painting.
- Dual-colored segments indicate chromosomes from different geographic regions. See an African American Man's painting.

Select a person: [African American Man ▼]

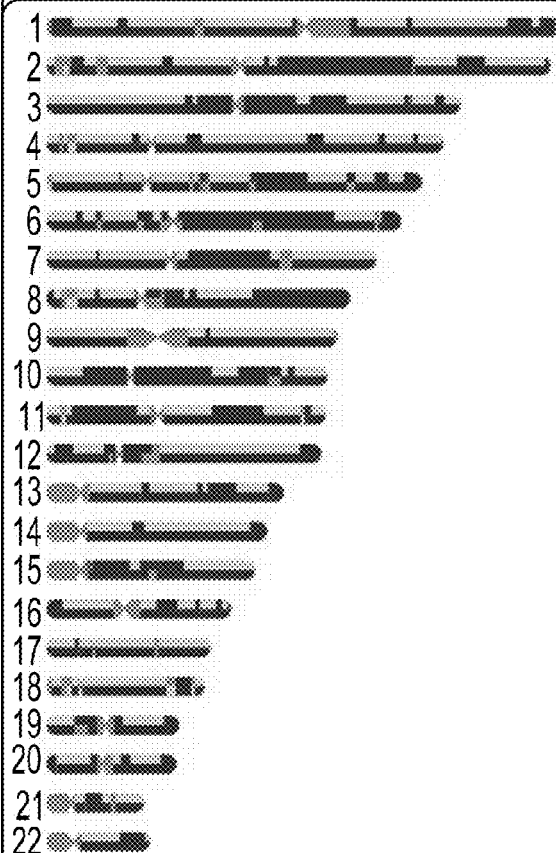

African American Man ⓘ

Most African Americans today trace a large part their ancestry to sub-Saharan Africa as a result of the slave trade. Over the generations since, both Europeans and Native Americans have intermarried with African Americans and contributed ancestry, as seen in the ancestry painting of this man, self-identified as African American. In fact, one of this man's chromosomes appears to be fully European across the whole genome, so it is likely that one of his parents was European.

- Europe 64%
- Africa 33%
- Asia 4%
- Not Genotyped

Worldwide Examples — 402

Click on the icons in the map below to see example painting of individuals from across the globe.

— 404

FIG. 4

1000 → Rates of Occurrence for Interval j on Chromosome i

Phased Case

| Value | African (AFR) | Asian (ASN) | European (EUR) |
|---|---|---|---|
| X | 0.12 | 0.02 | 0.85 |
| Y | 0.42 | 0.92 | 0.04 |
| Z | 0.46 | 0.06 | 0.11 |

1002 →

Unphased Case

| Pair Value | AFR/AFR | ASN/ASN | EUR/EUR | AFR/ASN | ASN/EUR | AFR/EUR |
|---|---|---|---|---|---|---|
| X/X | 0.0144 | 0.0004 | 0.7225 | 0.0024 | 0.017 | 0.102 |
| X/Y | 0.0504 | 0.0184 | 0.034 | 0.1104 | 0.0008 | 0.357 |
| X/Z | 0.0552 | 0.0012 | 0.0935 | 0.0072 | 0.0022 | 0.391 |
| Y/X | 0.0504 | 0.0184 | 0.034 | 0.0084 | 0.782 | 0.0048 |
| Y/Y | 0.1764 | 0.8464 | 0.0016 | 0.3864 | 0.0368 | 0.0168 |
| Y/Z | 0.1932 | 0.0552 | 0.0044 | 0.0252 | 0.1012 | 0.0184 |
| Z/X | 0.0552 | 0.0012 | 0.0935 | 0.0092 | 0.051 | 0.0132 |
| Z/Y | 0.1932 | 0.0552 | 0.0044 | 0.4232 | 0.0024 | 0.0462 |
| Z/Z | 0.2116 | 0.0036 | 0.0121 | 0.0276 | 0.0066 | 0.0506 |

1004 →

Unphased Case, Combined

| Pair Value | AFR/AFR | ASN/ASN | EUR/EUR | AFR/ASN | ASN/EUR | AFR/EUR |
|---|---|---|---|---|---|---|
| X/X | 0.0144 | 0.0004 | 0.7225 | 0.0024 | 0.017 | 0.102 |
| X/Y | 0.1008 | 0.0368 | 0.068 | 0.1188 | 0.7828 | 0.3618 |
| X/Z | 0.1104 | 0.0024 | 0.187 | 0.0164 | 0.0532 | 0.4042 |
| Y/Y | 0.1764 | 0.8464 | 0.0016 | 0.3864 | 0.0368 | 0.0168 |
| Y/Z | 0.3864 | 0.1104 | 0.0088 | 0.4484 | 0.1036 | 0.0646 |
| Z/Z | 0.2116 | 0.0036 | 0.0121 | 0.0276 | 0.0066 | 0.0506 |

FIG. 10A

Rates of Occurrence for Interval j on Chromosome i

1006 ⟶

Phased Case

| Value | African (AFR) | Asian (ASN) | European (EUR) |
|---|---|---|---|
| X | B5 | C5 | D5 |
| Y | B6 | C6 | D6 |
| Z | B7 | C7 | D7 |

1008 ⟶

Unphased Case

| Pair Value | AFR/AFR | ASN/ASN | EUR/EUR | AFR/ASN | ASN/EUR | AFR/EUR |
|---|---|---|---|---|---|---|
| X/X | =B5*B5 | =C5*C5 | =D5*D5 | =B5*C5 | =C5*D5 | =D5*B5 |
| X/Y | =B5*B6 | =C5*C6 | =D5*D6 | =B5*C6 | =C5*D6 | =D5*B6 |
| X/Z | =B5*B7 | =C5*C7 | =D5*D7 | =B5*C7 | =C5*D7 | =D5*B7 |
| Y/X | =B6*B5 | =C6*C5 | =D6*D5 | =B6*C5 | =C6*D5 | =D6*B5 |
| Y/Y | =B6*B6 | =C6*C6 | =D6*D6 | =B6*C6 | =C6*D6 | =D6*B6 |
| Y/Z | =B6*B7 | =C6*C7 | =D6*D7 | =B6*C7 | =C6*D7 | =D6*B7 |
| Z/X | =B7*B5 | =C7*C5 | =D7*D5 | =B7*C5 | =C7*D5 | =D7*B5 |
| Z/Y | =B7*B6 | =C7*C6 | =D7*D6 | =B7*C6 | =C7*D6 | =D7*B6 |
| Z/Z | =B7*B7 | =C7*C7 | =D7*D7 | =B7*C7 | =C7*D7 | =D7*B7 |

ANCESTRY PAINTING

INCORPORATION BY REFERENCE

An Application Data Sheet is filed concurrently with this specification as part of the present application. Each application that the present application claims benefit of or priority to as identified in the concurrently filed Application Data Sheet is incorporated by reference herein in their entireties and for all purposes.

SEQUENCE LISTING

This application contains a Sequence Listing which is submitted electronically in ASCII format and is hereby incorporated by reference in its entirety. Said ASCII copy, created on Feb. 25, 2022, is named 23MEP010C3_ST25.txt and is 1 KB in size.

BACKGROUND OF THE INVENTION

The instructions for making the cells in the human body are encoded in deoxyribonucleic acid (DNA). DNA is a long, ladder-shaped molecule, in which each corresponding rung is made up of a pair of interlocking units, called bases, that are designated by the four letters in the DNA alphabet—A, T, G and C. A always pairs with T, and G always pairs with C. The sequence that makes up an individual's DNA is referred to as the individual's genome.

The long molecules of DNA in cells are organized into pieces called chromosomes. Humans have 23 pairs of chromosomes. Chromosomes are further organized into short segments of DNA called genes. The different letters A, T, G, and C, which make up a gene, dictate how cells function and what traits to express by dictating what proteins the cells will make. Proteins do much of the work in the body's cells. Some proteins give cells their shape and structure. Others help cells carry out biological processes like digesting food or carrying oxygen in the blood. Using different combinations of the As, Cs, Ts and Gs, DNA creates the different proteins and regulates when and how they are turned on. Genetic or genotypic data includes information about an individual's DNA sequence, including his or her genome or particular regions of the genome. Regions of a particular individual's genome can also be referred to as DNA or genetic sequences.

Genotypic data includes single nucleotide polymorphisms (SNPs), which are the variations in the DNA sequence that occur at particular locations in an individual's DNA sequence. SNPs can generate biological variation between people by causing differences in the genetic recipes for proteins. Different variants of each SNP are called alleles. Those differences can in turn influence a variety of traits such as appearance, disease susceptibility or response to drugs. While some SNPs lead to differences in health or physical appearance, some SNPs seem to lead to no observable differences between people at all.

Unlike the sex chromosomes and the mitochondrial DNA, which are inherited as blocks, the 22 biparental chromosomes, known as autosomes, are scrambled during reproduction. Through a process known as recombination, each parent pulls his or her paired set of 22 autosomes into chunks, then reassembles a new single set using half the material from each pair. The two single sets of chromosomes from each parent are combined into a new paired set when a sperm fertilizes an egg. Every region of a person's autosomes (non-sex chromosomes) is represented by a pair of DNA sequences, one inherited from the mother and one from the father.

Scientific research today shows that the family trees of all humans living today lead back to an African homeland about 200,000 years ago. The more recent heritage of an individual's chromosomes, however, may have arisen from a population associated with a pre-colonial (before the era of intercontinental travel) home continent, such as Africa, Asia or Europe.

BRIEF DESCRIPTION OF THE DRAWINGS

The file of this patent contains at least one drawing executed in color. Copies of this patent with color drawings will be provided by the Patent and Trademark Office upon request and payment of the necessary fee.

Various embodiments of the invention are disclosed in the following detailed description and the accompanying drawings.

FIG. 1 is a diagram illustrating an embodiment of a display of ancestral data for an individual of European descent.

FIG. 2 is a diagram illustrating an embodiment of a display of ancestral data for an individual of European descent, including a pull-down menu.

FIG. 4 is a diagram illustrating an embodiment of a display of ancestral data for an individual of African American descent.

FIG. 10A illustrates examples of genotype frequency tables.

For clarity, FIG. 10B illustrates how the values are obtained when going from table 1000 to table 1002.

FIG. 12 is a diagram illustrating an embodiment of a sliding window used to smooth out ancestral origin assignments.

DETAILED DESCRIPTION

Figure 3:
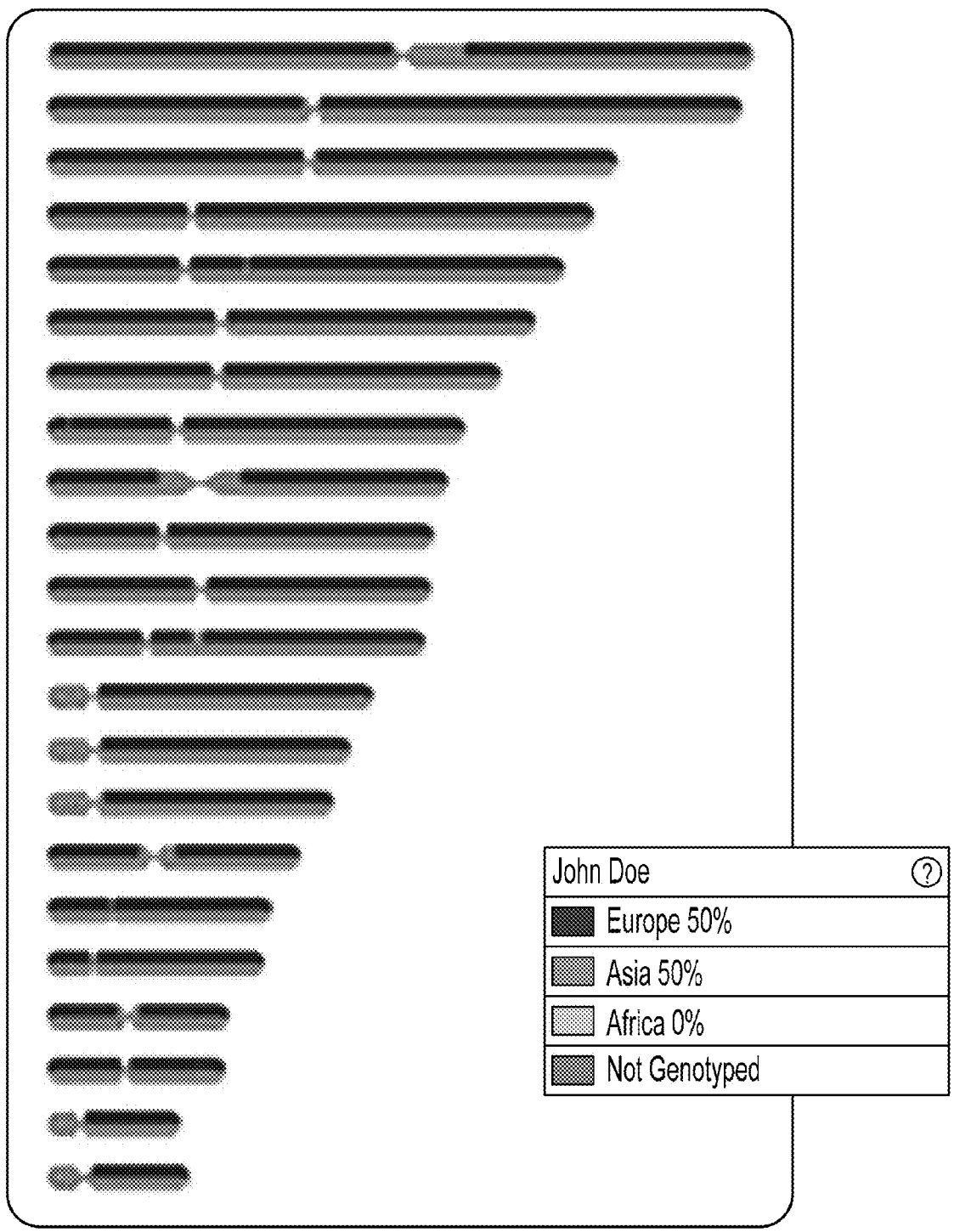
FIG. 3 is a diagram illustrating an embodiment of a display of ancestral data for an individual of Asian and European descent.

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

FIG. 1 is a diagram illustrating an embodiment of a display of ancestral data for an individual of European descent. Display 100 indicates ancestral origins for Greg Mendel, an example individual whose parents and grandparents are of European descent. Three of his grandparents are German and one is Norwegian.

In display 100, the 22 chromosomes are graphically displayed and each interval of each chromosome is colored according to legend 102. In this example, blue indicates European ancestral origin, orange indicates Asian ancestral origin, green indicates African ancestral origin, and gray indicates that that interval has not been genotyped. For example, a genotyping chip might have no or few markers present at those regions of the genome. Display 100 shows an example of ancestry painting, in which color is used to "paint" ancestral origins. This painting technique allows ancestral data to be conveyed to a user in a way that is easy and intuitive to understand. Although color may be described in the examples herein, in various embodiments, any other type of fill may be used, such as shading, hatching, or other patterns. In some embodiments, other visual cues besides color or fill may be used to display ancestral origins.

Although every person has two copies of each chromosome—one from the mother and one from the father—this display depicts only one set of chromosomes in order to make it easier to read. Thus, each single chromosome drawn in the painting really represents the composition of two paired chromosomes, as will be more fully illustrated below.

As shown in legend 102, Greg Mendel's 22 autosomes have 100% European ancestral origin. In some embodiments, this percentage is determined by adding up the lengths of the segments attributed to each population, as displayed, and then dividing by the total length. The numbers may be rounded to the nearest whole number. In this example, the grayed out regions are not genotyped and therefore not included in the percentage calculations.

Map 104 includes icons placed at various regions across the globe. Clicking on an icon causes the display to depict ancestral data for an example individual from the region where the icon is located. Examples of this are more fully described below.

Although the examples herein may show and describe autosomes (the non-sex chromosomes), in various embodiments, these techniques may be applied to one or more of the X chromosome, Y chromosome, mitochondrial genome, or any other appropriate genetic regions.

FIG. 2 is a diagram illustrating an embodiment of a display of ancestral data for an individual of European descent, including a pull-down menu. Display 200 shows display 100 after a user has selected pull-down menu 202. Pull-down menu 202 includes a list of individuals from which to select. In some embodiments, the list includes individuals who have allowed sharing of their genetic data with the user. Some individuals in the list are not identified by name, such as "African American Man" or "Uyghur Woman." These are unidentified individuals that are provided as examples for illustrative purposes. The anonymous Italian, Cambodian, and Senegalese sample individuals have similarly uniform paintings to Greg Mendel's.

FIG. 3 is a diagram illustrating an embodiment of a display of ancestral data for an individual of Asian and European descent. Display 300 indicates ancestral origins for John Doe, an individual who has a mother of Chinese ancestry and a father of Northern European ancestry.

In display 300, each chromosome is displayed as half orange and half blue, an indication that one autosome of each pair originated in Europe and the other in Asia. Suppose John Doe had a daughter with a woman of Chinese ancestry. The child would get 22 autosomes from her mother. So one half of each chromosome in her display would be solid orange. The other half would be a roughly 50/50 mix of orange and blue bands—a reflection of her father's half-European, half-Asian ancestry.

If one were to follow the same family over the years, each new generation's ancestry paintings would grow more or less colorful depending on the continental diversity of their parents, grandparents, and so on. If no more people of non-Asian descent joined the pedigree, recombination would repeatedly cut up the blue chunks of DNA, shortening them by half each time, until after about four generations they would become indistinguishable from random noise. People with relatively recent ancestry tracing to two or more continents tend to have the most colorful paintings.

FIG. 4 is a diagram illustrating an embodiment of a display of ancestral data for an individual of African American descent. Display 400 indicates ancestral origins for an African American man. For example, display 400 may be displayed in response to a user selecting "African American Man" from menu 202. Also, display 400 may be displayed in response to a user selecting an icon corresponding to an African American (one of the icons in North America) in map 104.

Most African Americans have ancestry from both Europe and Africa. As a result, their ancestry paintings are mostly a mixture of navy and green (as shown), though the relative proportion of the two colors can vary widely.

There may be some small amount of noise present in the painting of a person's recent (the last 500 years or so) ancestry. In this example, there are a few brief stretches of orange (meaning Asian ancestry), as shown. The orange stretches are likely statistical noise rather than indicators of true Asian descent.

Legend 402 indicates that along each of the chromosomes, when the contributions of each region are summed, 64% of this African American's genome traces to European ancestors, 33% to Africans, and 4% Asians (which is likely noise). The gray intervals, such as the one at the left end of chromosome 13, are regions where the genotyping chip has no markers. These regions are not included in calculating the percentages.

Map 404 includes icons placed at various regions across the globe. The selected icon (highlighted in blue) is associated with an African American. Clicking on an icon causes the display to depict ancestral data for an example individual from the region where the icon is located.

Figure 5:
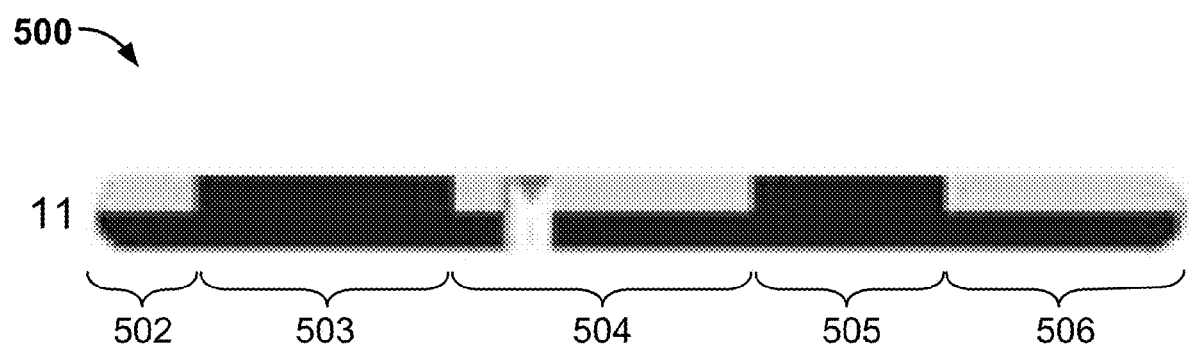
FIG. 5 is a diagram illustrating an embodiment of a display of ancestral data associated with a chromosome.

FIG. 5 is a diagram illustrating an embodiment of a display of ancestral data associated with a chromosome. Display 500 is an example display of ancestral data associated with chromosome 11. Display 500 includes five intervals across its length—intervals 502-506. Each interval is divided into an upper half and a bottom half. Each half represents a segment in a chromosome pair, where one segment is inherited from the mother and the other segment in the pair is inherited from the father of the individual. Each half is colored according to an ancestral origin associated with one parent. For example, in this case, two of them (intervals 503 and 505) are blue in both the top and bottom halves, meaning that this man inherited DNA tracing to European ancestors from both his mother and father. The other three intervals (intervals 502, 504, and 506) are each half blue and half green. That means in those locations, one copy of this man's DNA traces back to a European ancestor who lived in the last few hundred years, the other to an African ancestor. Thus, as depicted in this display, one interval along the graphical chromosome represents a pair of chromosome segments in a real chromosome.

In some embodiments, the ancestral data is unphased. In other words, it is not known which parent a particular segment of autosome came from. In any two-color interval, it is not indicated whether the top half or the bottom half was inherited from the mother or father. In some embodiments, when the ancestral data is unphased, the colors are ordered and the top half is colored with the color that is higher in order. For example, the order may be: Asia, Africa, Europe. In this case, orange will always be on top of green, which will always be on top of blue.

In some embodiments, the ancestral data is phased. Phased means that the individual's diploid genotype is resolved into two haplotypes, one for each chromosome. In other words, it is known from which parent a particular segment of autosome was inherited. For example, the top half may show the ancestral origins from the mother and the bottom half may show the ancestral origins from the father, or vice versa.

Figure 6:
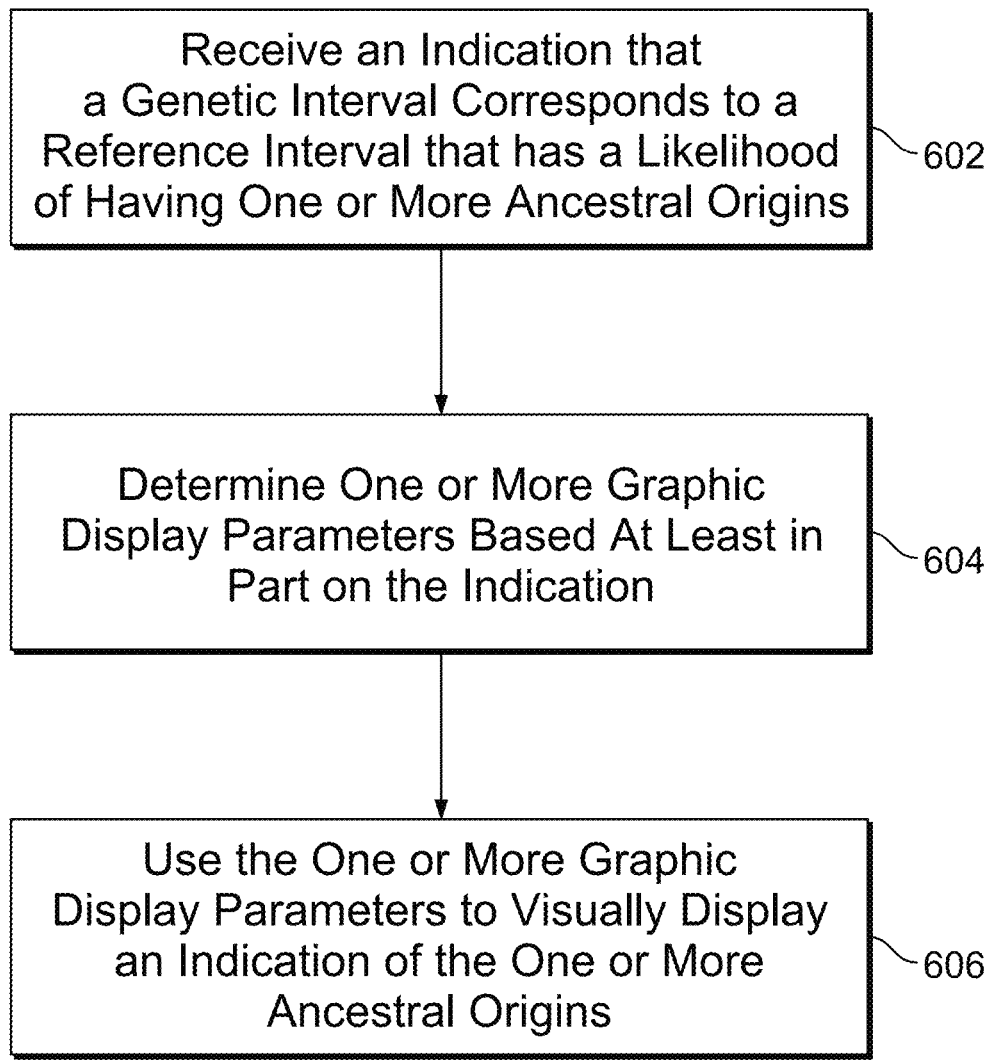
FIG. 6 is a flow chart illustrating an embodiment of a process for displaying ancestral data.

FIG. 6 is a flow chart illustrating an embodiment of a process for displaying ancestral data. For example, this process may be used to display any one of displays 100-500.

At 602, an indication that a genetic interval corresponds (e.g., matches) a reference interval that has a likelihood of having one or more ancestral origins is received. Depending on the embodiment, a genetic interval may include a chromosome segment (haploid) or a pair of chromosome segments (diploid). Thus, a genetic interval may be associated with one or two ancestral origins. A segment may include a sequence or set of SNPs along a chromosome. Examples of intervals include intervals 502-506. A reference interval is a genetic interval that has a likelihood of having one or more ancestral origins. For example, the likelihood may be determined based on a database of reference individuals who have known ancestral origins.

At 604, one or more graphic display parameters are determined based at least in part on the indication. Examples of the graphic display parameters include different colors (or visual patterns) that correspond to ancestral origins. For example, if the indication is that the genetic interval matches a reference interval that has a 90% likelihood of having African and Asian origin, then in some embodiments, it is determined that green and orange are graphical display parameters. In other embodiments, it might be determined that blue is a graphical display parameter, for example, based on the fact that neighboring intervals have a high likelihood of having European origin. In various embodiments, a variety of techniques may be used to obtain a graphic display parameter, as more fully described below.

At 606, one or more graphic display parameters are used to visually display an indication of the one or more ancestral origins. For example, if the graphical display parameters are blue and green, than an interval is painted blue and green, such as interval 502 in display 500.

Figure 7:
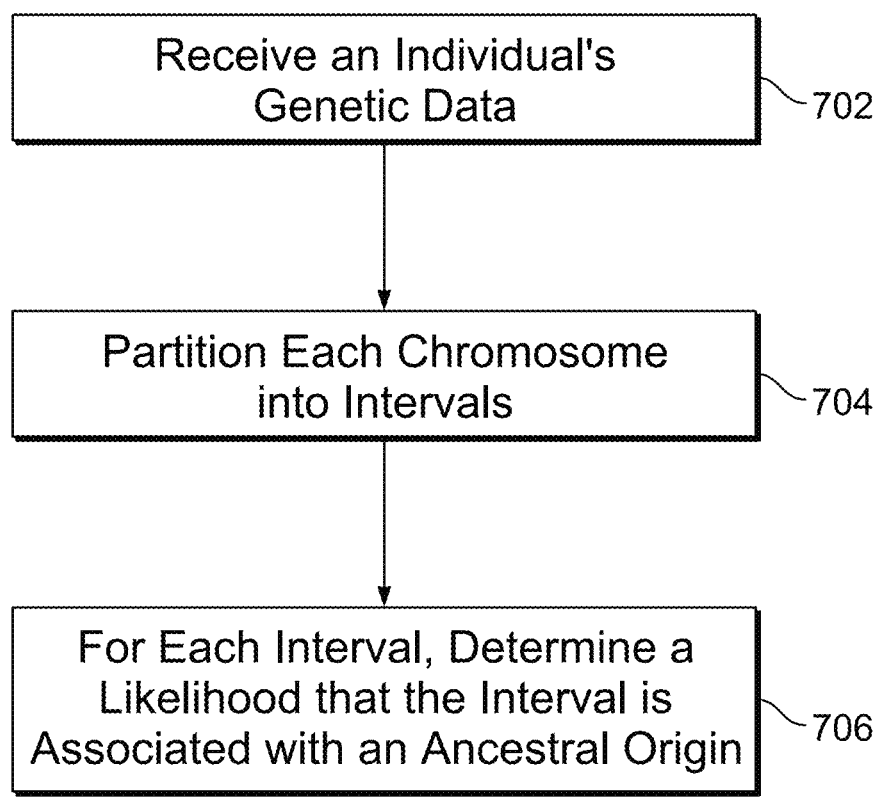
FIG. 7 is a flow chart illustrating an embodiment of a process for receiving an indication that a genetic interval matches a reference interval that has a likelihood of having one or more ancestral origins.

FIG. 7 is a flow chart illustrating an embodiment of a process for receiving an indication that a genetic interval matches a reference interval that has a likelihood of having one or more ancestral origins. For example, this process may be used to perform 602.

At 702, an individual's phased or unphased genetic data is received. For example, a genotyping chip, such as the Illumina HumanHap550v3 genotyping chip, may be used to assay an individual's genotype. As an example, genetic data for each of the non-gray segments shown in display 100 is obtained for an individual. The genetic data may be phased or unphased. If it is phased, then information regarding whether each location in a segment is inherited from the mother or the father of the individual is known. In some embodiments, phasing is performed using BEAGLE software, developed by Brian and Sharon Browning at the University of Auckland. Phasing can also be performed for an individual if the genetic data of one or both parents is known. Phasing refers to resolving an individual's diploid genotype into two haplotypes, one for each chromosome. In some embodiments, phased data includes data for one chromosome segment and an indication of a parent from which the data was inherited, and unphased data includes data for two corresponding chromosome segments in a pair of chromosome segments without an indication of a parent from which the data was inherited because this has not been determined. In the case of phased data, it is not necessarily known from which parent (mother or father) a phased chromosome segment comes from, in the absence of genetic data from the mother and/or father. What is known is that one phased segment came from one parent, and the homologous segment came from the other parent.

At 704, each chromosome is partitioned into intervals. In some embodiments, the intervals correspond to intervals in a table of genotype frequencies, as more fully described below. The interval may include diploid data or haploid data, depending on whether the data is phased or unphased. For example, in the case of phased data, each chromosome is partitioned into segments, e.g., of consecutive SNPs. In the case of unphased data, each chromosome pair is partitioned into segment pairs, e.g., of consecutive SNPs.

At 706, for each interval, likelihood that the interval is associated with an ancestral origin is determined. In the cased of phased data, a likelihood that the segment is associated with an ancestral origin is determined. In the case of unphased data, likelihood that the segment pair is associated with an ancestral origin is determined. In some embodiments, the likelihood is determined by looking up the interval in a table of genotype frequencies, as more fully described below.

Figure 8:
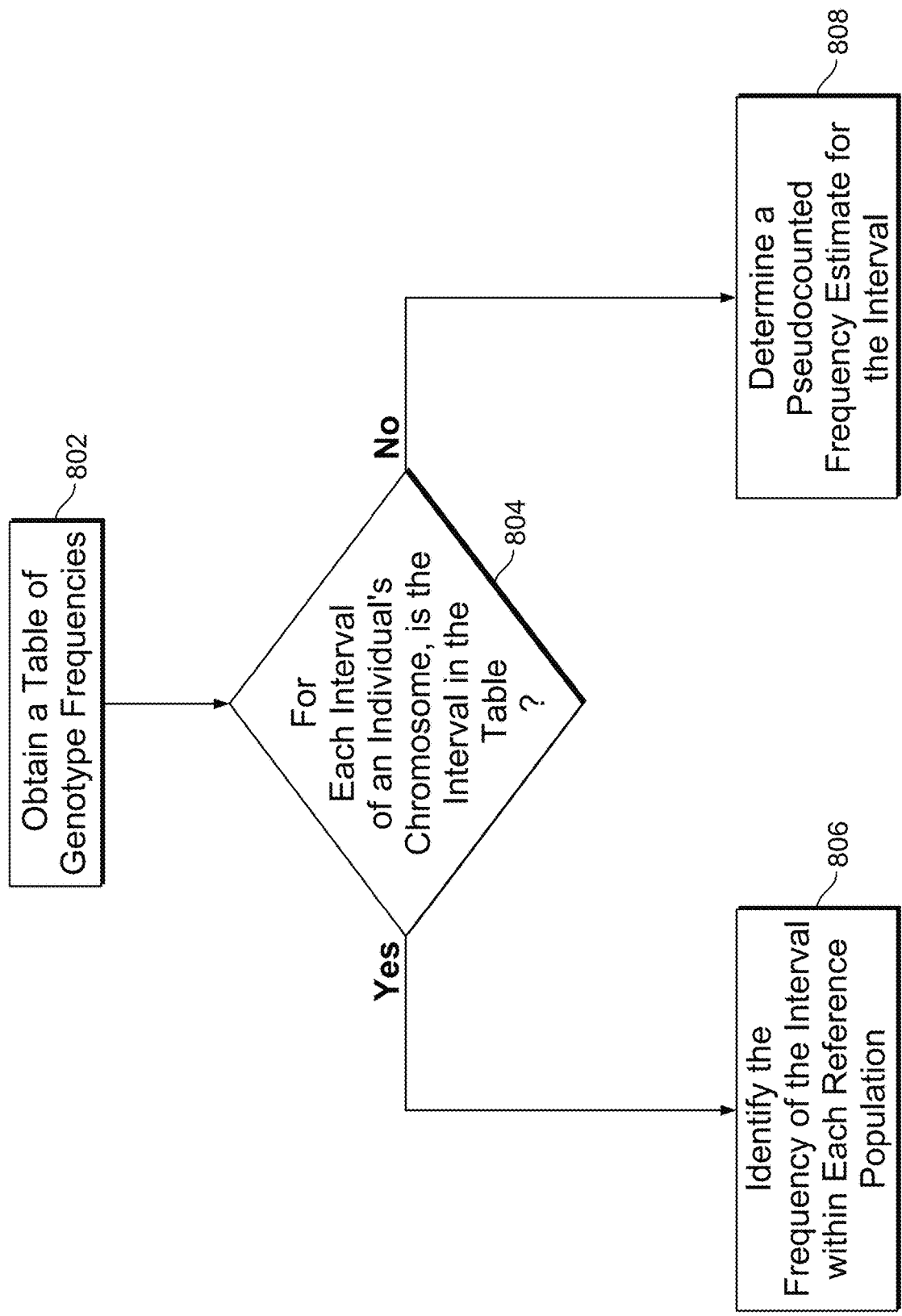
FIG. 8 is a flow chart illustrating an embodiment of a process for determining a likelihood that a genetic interval is associated with an ancestral origin.

FIG. 8 is a flow chart illustrating an embodiment of a process for determining likelihood that a genetic interval is associated with an ancestral origin. For example, this process may be used to perform 706. At 802, a database of genotype frequencies is obtained. In some embodiments, the database includes a table that maps a list of known genetic intervals to the corresponding frequencies of the genetic intervals within reference populations. In some embodiments, the table includes all possible genotypes of each interval within each reference population and the fraction of that population having that genotype. The fraction of a population having a genotype may also be referred to as the frequency or rate (of occurrence) of a genotype within a population. In the case of phased data, the reference populations include single ancestral origins to correspond to a segment of a single chromosome. In the case of unphased data, the reference populations include all combinations of two ancestral origins to correspond to a pair of segments from two chromosomes, as more fully described below.

At 804, for each interval of an individual's chromosome, an estimate of the frequency with which that interval is observed in the several reference populations is looked up in a table constructed for this purpose. The estimation method takes the reference population sample size into account, so that intervals not observed in the reference populations receive frequency estimates with small positive values instead of zero. In some embodiments, a pseudocounted frequency value of 0 is replaced with a small nonzero number because a frequency of 0 would be problematic in some implementations (e.g., implementations that include a division by 0). In some embodiments, at 808, the frequency is set equal to 0.

In some embodiments, 804 and 806 are repeated for all intervals until likelihood is determined for all intervals of the individual's genotyped data.

Figure 9:
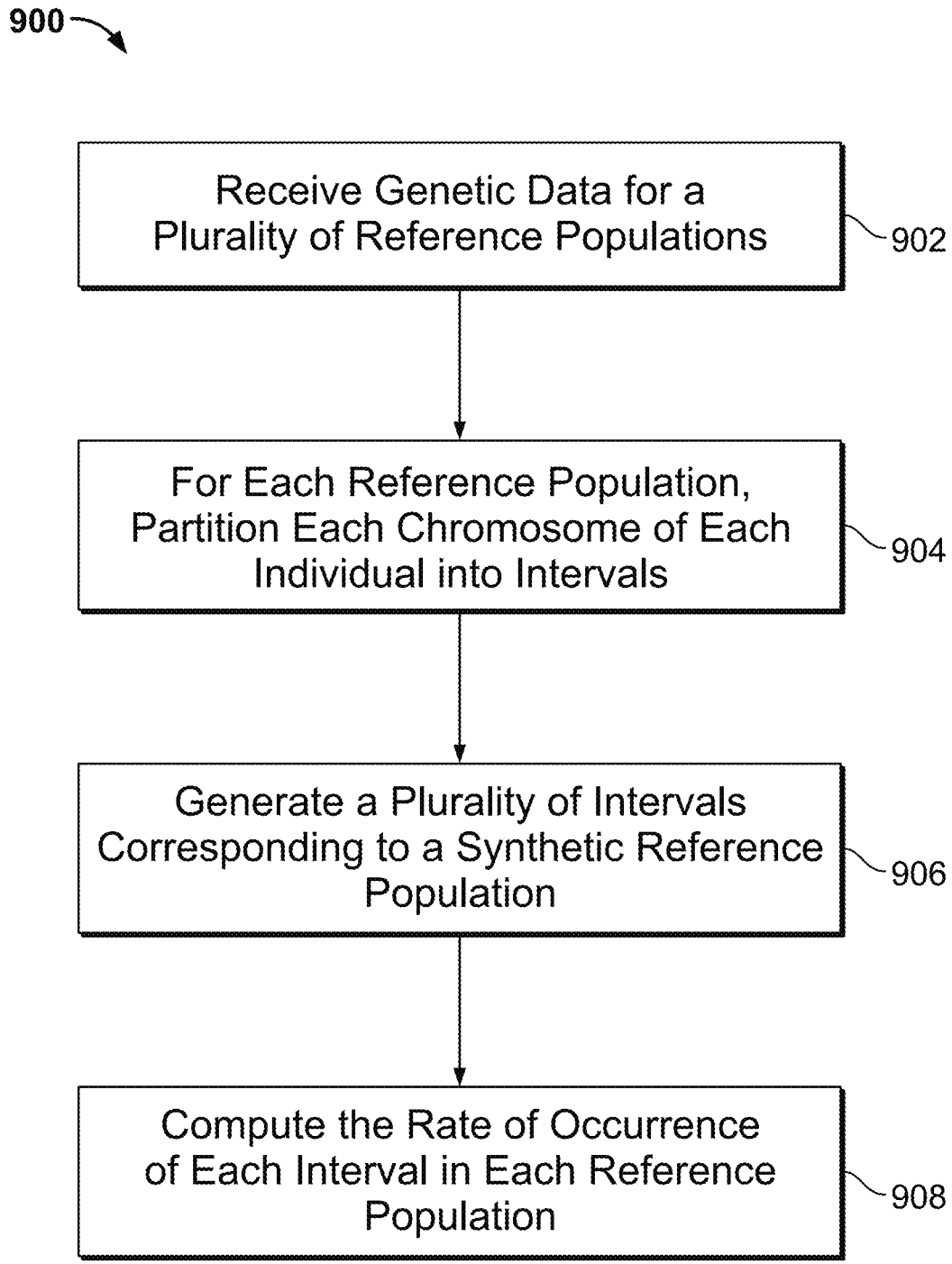
FIG. 9 is a flow chart illustrating an embodiment of a process for creating a table of genotype frequencies.

FIG. 9 is a flow chart illustrating an embodiment of a process for creating a table of genotype frequencies. For example, such a table may be obtained at 802. At 902, genetic data for a plurality of reference populations is received from one or more sources. For example, data may be obtained from sources such as the Centre d'Etude du Polymorphisme Humain (CEPH) Human Genodiversity Project or the International HapMap Project (www.hapmap.org).

In some embodiments, the data may be obtained from a database associated with a website that allows individuals to view and/or share with other users their genetic data. An example of such a website is www.23andme.com. Each user may provide data regarding their ancestral origin.

At 904, for each reference population, each chromosome of each reference individual is partitioned into intervals. In some embodiments, the intervals are nonoverlapping, adjacent words of consecutive SNPs, or points along the genome where individuals may differ. In some embodiments, the intervals overlap. In some embodiments, words of a fixed number of SNPs, such as ten SNPs are used. In some embodiments, words spanning a minimum genetic distance, e.g., 0.010 cM, as defined by the fine scale recombination map found at HapMap, are used with a threshold on the minimum number of SNPs per word.

If the data is unphased and reference populations of individuals of mixed ancestry are not available, then in some embodiments, at 906, a plurality of intervals corresponding to a synthetic reference population of synthetic individuals are generated from a population of real individuals, as more fully described below.

At 908, a rate of occurrence of each interval in each reference population is computed, which is also more fully described below.

FIG. 10A illustrates examples of genotype frequency tables. For example, these tables may be obtained at 802 and/or created by process 900. In this example, there are three reference populations: African (AFR), East Asian (ASN), and European (EUR).

Table 1000 is an example of a genotype frequency table for a particular interval j on a particular chromosome i, for the case of phased data. For the case of phased data, each interval is a segment. The possible values of the segment j on chromosome i in this example are: X, Y, and Z. For example, X may be ACAAGTACCTTGAAAAAATTT (SEQ ID NO: 1). In some embodiments, the genotype frequencies (i.e., 0.12, 0.42, 0.46, 0.02, 0.92, 0.06, 0.85, 0.04, and 0.11) are obtained according to 908 or as follows: For each reference population, for each value X, Y, and Z, the number of individuals in that reference population having that value at segment j, chromosome i, is determined. The number of individuals is divided by the total number of individuals in that reference population to obtain the genotype frequency. For example, if there are 100 African individuals in the reference population and 12 of those individuals have genotype X at interval j on chromosome i, then the genotype frequency would be 12/100=0.12, as shown in table 1000. As shown, each column in table 1000 sums to 1.

Table 1004 is an example of a genotype frequency table for a particular interval j on a particular chromosome i, for the case of unphased data.

The data in table 1002 is discussed first. For the case of unphased data, each interval is a segment pair. In this example, the possible values of each segment are X, Y, and Z (as in table 1000). Therefore, the possible values of the segment pair j on chromosome i in this example are all possible combinations of X, Y, and Z: X/X, X/Y, Y/X, Y/Y, Y/Z, Z/X, Z/Y, and Z/Z. For example, X/X may be the pair ACAAGTACCTTGAAAAAATTT (SEQ ID NO: 1)/ACAAGTACCTTGAAAAAATTT (SEQ ID NO: 1). This is an example of generating a plurality of intervals corresponding to a synthetic reference population, or 906.

The possible reference populations are African/African, East Asian/East Asian, European/European, African/East Asian, African/European, and East Asian/European. The frequency of each segment pair value is determined by taking the product of the frequencies of the individual segments within a reference population. For example, the frequency of X in an African population (0.12) times the frequency of Y in an East Asian population (0.92) equals the frequency of X/Y in an African/East Asian synthetic population (0.1104). Because the data is unphased and there is no distinction between X/Y and Y/X, for each possible reference population, the frequency of X/Y and the frequency of Y/X can be summed under X/Y. For example, 0.1104 is summed with 0.0084 to produce 0.1188 for the above example. The same is true for X/Z and Z/X, and for Y/Z and Z/Y. This produces table 1004. This is an example of computing the rate of occurrence of each interval in each reference population, or 908.

For clarity, FIG. 10B illustrates how the values are obtained when going from table 1000 to table 1002. In this example, table 1006 shows table 1000 with variables B5-B7, C5-C7, and D5-D7 in each cell. Table 1008 shows how the frequencies from table 1006 are combined to produce the frequencies of the combinations shown in table 1002.

In some embodiments, the reference populations include individuals of mixed ancestry, and there is no need to generate synthetic reference populations. In this case, the genotype frequencies in table 1004 may be obtained as follows: For each reference population, for each possible value X/X, X/Y, X/Z, Y/Y, Y/Z, and Z/Z, the number of individuals in that reference population having that value at segment pair j, chromosome i, is determined. The number of individuals is divided by the total number of individuals in that reference population to obtain the genotype frequency. For example, if there are 1000 Asian/European individuals in the reference population and 17 of those individuals have genotype X/X at interval j on chromosome i, then the genotype frequency would be 17/1000=0.017, as shown in table 1004.

In some embodiments, some combination of synthetic and real reference populations is used to obtain the genotype frequencies in table 1004.

Tables 1000 and 1004 are examples of genotype frequency tables for a particular interval j on a particular chromosome i. In some embodiments, to display an indication of ancestral data for all 22 autosomes, there is a table for each interval on each chromosome. In some embodiments, as previously described, data is not available for all intervals since some genotyping chips do not have or have few markers in some segments. In various embodiments, data may be organized in a variety of ways. For example, the number of tables used may vary and/or other data structures besides tables may be used. In some embodiments, the data is implemented as a hash table for ease of lookup. Any appropriate type of lookup table may be used in various embodiments.

In addition, a variety of techniques may be used to obtain genotype frequencies. In various embodiments, any appropriate technique to obtain genotype frequencies may be used.

Figure 11:
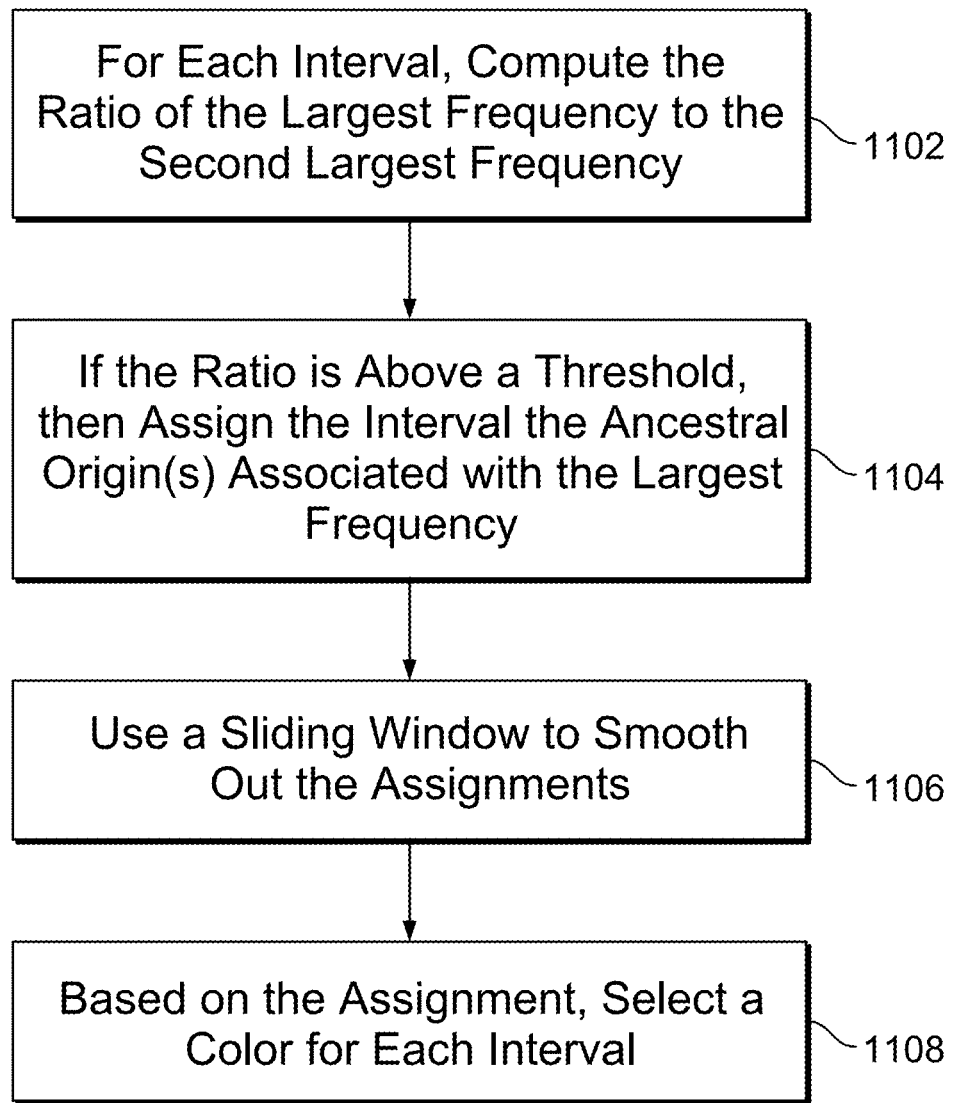
FIG. 11 is a flow chart illustrating an embodiment of a process for determining one or more graphic display parameters.

FIG. 11 is a flow chart illustrating an embodiment of a process for determining one or more graphic display parameters. For example, this process may be used to perform 604. At 1102, for each interval, the ratio of the largest frequency to the second largest frequency is computed. For example, a particular individual Greg has genotype X at interval j on chromosome i. (This is a phased example.) The frequencies associated with genotype X according to table 1000 are: AFR 0.12, ASN 0.02, and EUR 0.85. The ratio of the largest frequency to the second largest frequency is 0.85/0.12=7.08. At 1104, if the ratio is above a given threshold or above a given quantile, then the ancestral origin(s) associated with the largest frequency is assigned to the interval. In the above example, the ratio for Greg is 7.08. If the threshold is 5, then because 7.08>5, the ancestral origin of EUR is assigned to the interval j on chromosome i for Greg. If the threshold is 10, then the interval is unassigned. At 1106, a sliding window is used to fill in and/or smooth out the assignments. In various embodiments, this step is skipped or other types of smoothing or post processing are performed. As a result of the smoothing, an assignment of EUR may be changed to a different ancestral origin assignment, such as ASN. An example of how a sliding window fills in and/or smooths out assignments is more fully described below. At 1108, based on the final assignment, a graphic display parameter is selected for each interval. For example, a color is selected, where different colors correspond to different ancestral origins. In Greg's case, for interval j on chromosome i, if the assignment remains EUR after the processing of 1106, the color blue is selected for interval j on chromosome i. This is shown in display 100, where blue corresponds to European ancestral origin.

Figure 12:
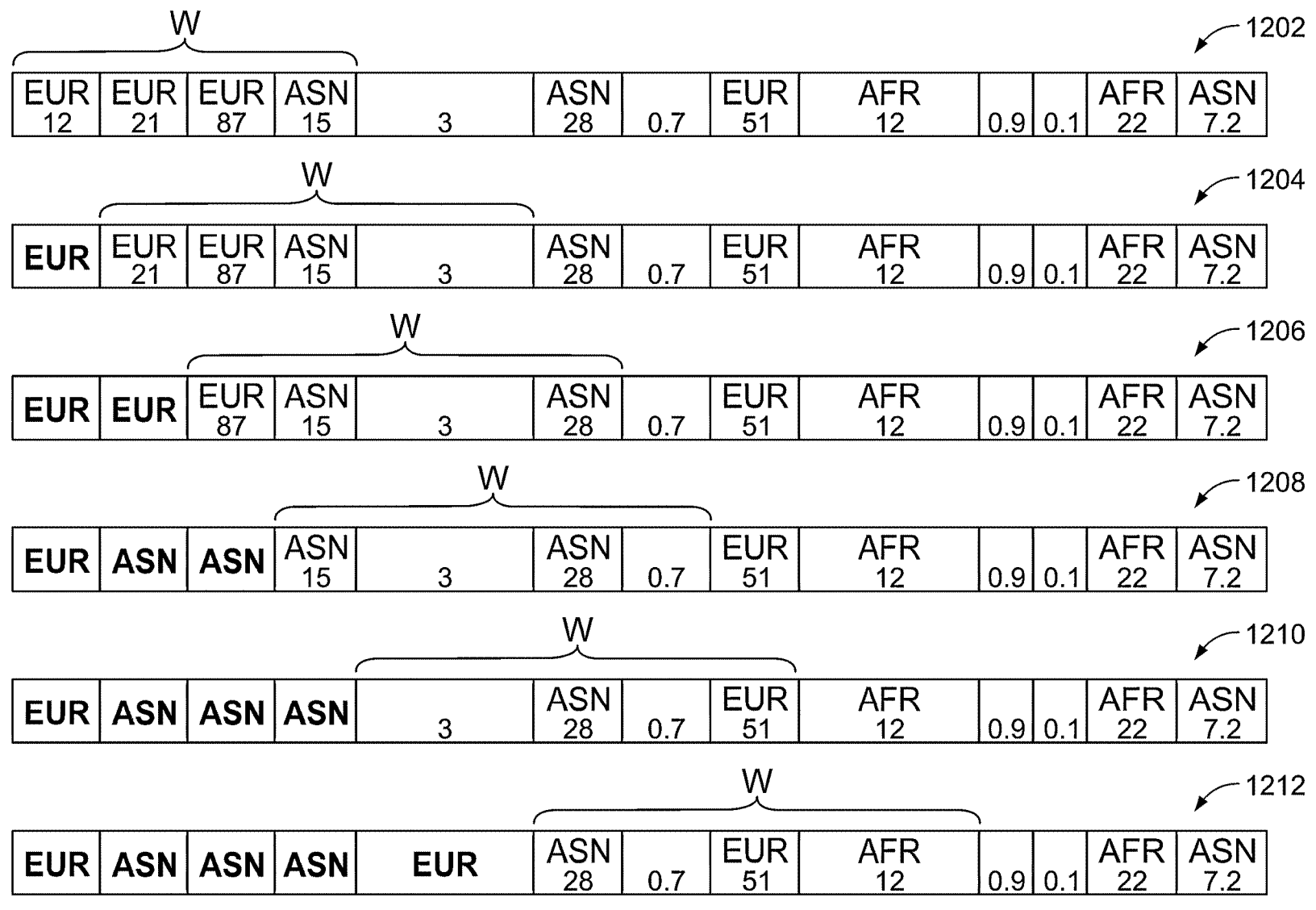

FIG. 12 is a diagram illustrating an embodiment of a sliding window used to smooth out ancestral origin assignments. In some embodiments, a dominant ancestral origin of a sliding window is estimated based on the segments in the sliding window, and that dominant ancestral origin is assigned to the first segment. The window slides by a segment, and the dominant ancestral origin of the segments in the sliding window is assigned to the second segment. In some embodiments, the dominant ancestral origin is estimated at least in part by determining the ancestral origin assigned to the majority of the segments in the sliding window.

Diagram 1202 illustrates consecutive segments of a chromosome, their assignments after 1104 and the ratio of the largest frequency to the second largest frequency for each. In this example, the threshold is 5. Therefore, if the ratio is below 5, an assignment was not made. A window of length W segments is used. In this example, W=4. In various embodiments W may be any appropriate length, such as 10-50. In some embodiments, the window length varies depending on the individual and/or chromosome. For example, if the assigned segments of a chromosome of an individual are all EUR, then the window length may be longer than if they are a mix of EUR and ASN. In diagram 1202, the window includes the first four segments with assignments EUR, EUR, EUR, and ASN. The majority is EUR, and so the first segment remains EUR, as shown in diagram 1204. In diagram 1204, the window has moved by one segment. The window now includes EUR, EUR, and ASN. The fifth segment does not count towards the vote because its ratio, 3, is below the threshold of 5. The majority is EUR, and so the second segment is still assigned EUR, as shown in diagram 1206. Similarly, at 1208, the third segment is assigned ASN. At 1210, the fourth segment is assigned ASN. At 1210, the window includes ASN and EUR, which is a tie. In some embodiments, the tie is broken by the segment with the higher ratio, in this case EUR with a ratio of 51, as shown at 1212. Ties may be broken in various ways in various embodiments.

In some embodiments, the window slides by more than one segment at a time. The distance by which a window slides each time is referred to as a slide length. A frame of segments is assigned the same ancestral origin at a time, where the frame has a length equal to the slide length. This may be the case because, depending on the display resolution, it may not be possible to display the ancestral origins at as fine a granularity as the segments. Therefore, it may be desirable to choose a slide length that is appropriate for the display resolution.

Other examples of post processing that may be performed at 1106 include sweeping for sharp discontinuities. For example, for each frame, if the neighboring frames have the same ancestral pair assignment, and it disagrees sharply with the ancestral-pair assignment of the frame, that frame is reverted to the ancestral-pair assignment of its neighbors. A sharp disagreement may be defined as one in which the intersection of the ancestral pairs is empty. This is seen in an example: frame 1 is African-European and frame 2 is Asian-Asian. Since frame 1 and frame 2 have no ancestry in common, i.e., their intersection is empty, the transition from frame 1 to frame 2 is sharp. If frame 1 were African-European and frame 2 were Asian-European, the intersection is "European", so the transition is not sharp.

Figure 13:
FIG. 13 is a diagram illustrating an embodiment of a karyotype view of a display of ancestral data for an individual.

FIG. 13 is a diagram illustrating an embodiment of a karyotype view of a display of ancestral data for an individual. This view shows the 22 autosomes. In some embodiments, the X chromosome is also shown. This view shows African, Asian, and European segments. In some embodiments, instead of dividing the individual's genome into African, Asian, and European segments, the karyotype view shows seven populations at the continental level. In some embodiments, the user can also choose to display the results corresponding to ancestral origins at the continental scale, regional scale (e.g., Northern Europe, East Africa, Western China), or subregional/local (e.g., a country, such as Ukraine or Ireland, or an ethnic group, such as Cherokee or Han). In some embodiments, by default, segments are displayed corresponding to the finest scale assignment that has been made. Display 1300 may also show and "paint" the user's Y chromosome (if male) and mitochondrial genome on the same display. As the Y and mitochondrion are each inherited as one indivisible unit of DNA sequence (without recombination), the painting procedure can match the DNA sequence to the ancestral origin where the DNA sequence is the most common.

Figure 14:
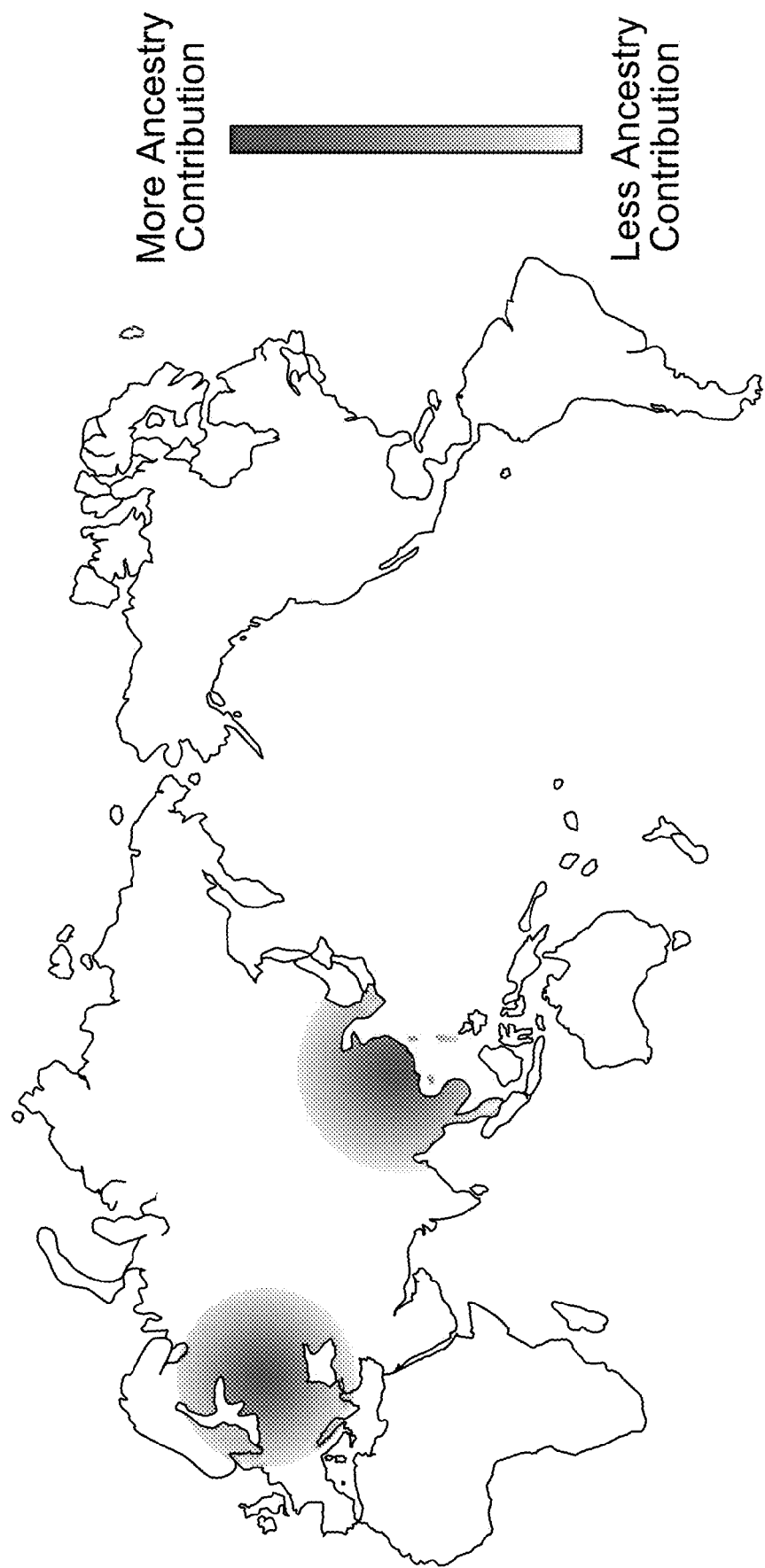
FIG. 14 is a diagram illustrating an embodiment of a personal landscape view of a display of ancestral data for an individual of Eastern European and East Asian ancestry.

FIG. 14 is a diagram illustrating an embodiment of a personal landscape view of a display of ancestral data for an individual of Eastern European and East Asian ancestry. This view uses the user's inferred ancestry to construct a spatial distribution showing where their ancestors are likely to have lived.

The blue discs on the world map indicate that this user has substantial ancestry deriving from Eastern Europe and East Asia. The intensity of the color encodes the proportion of the user's genome derived from that location on the Earth's surface. Alternatively, a contour plot or another density plot could be used. This painting would be expected for an individual having an Eastern European father and a Chinese mother.

Figure 15:
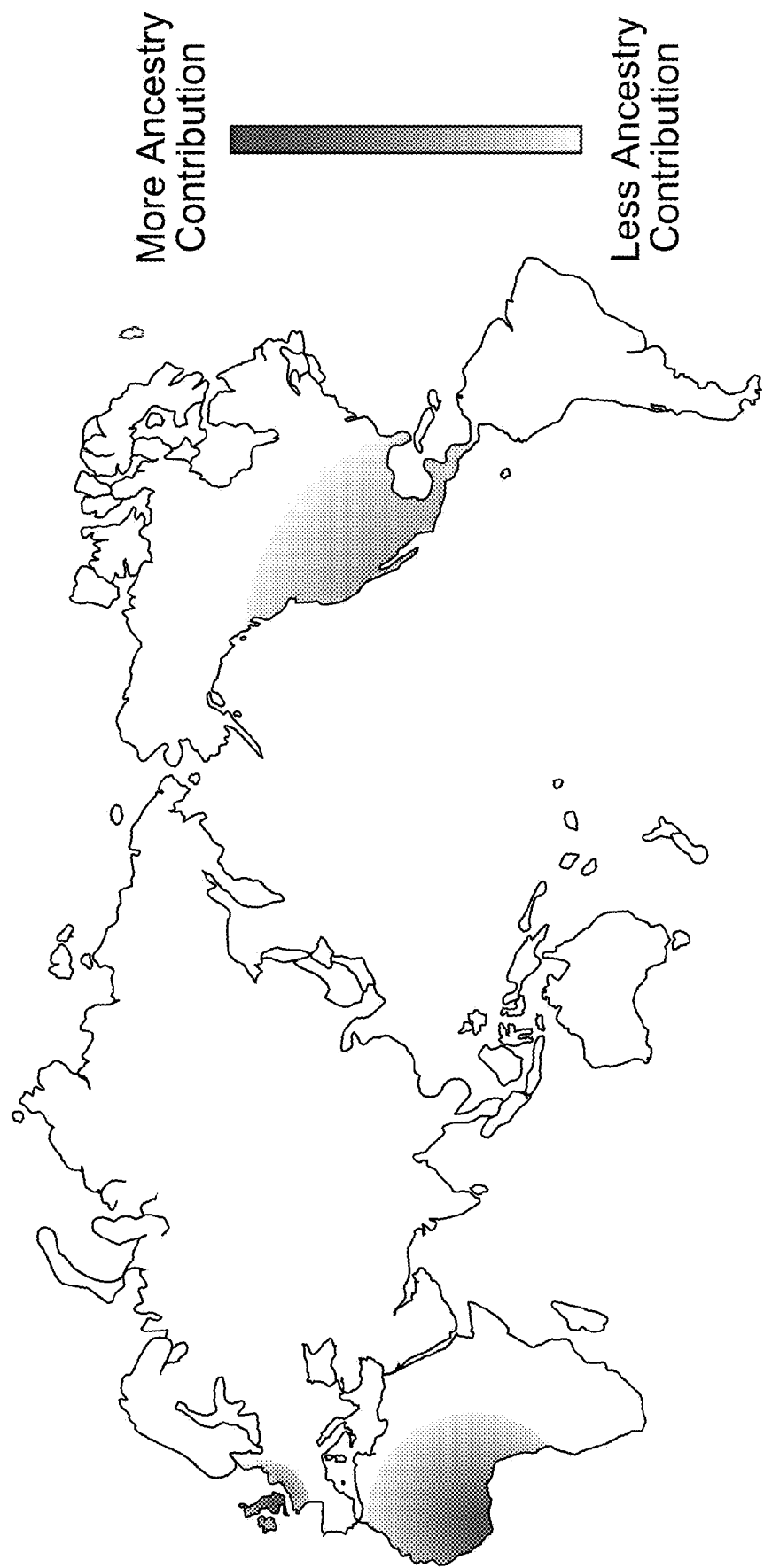
FIG. 15 is a diagram illustrating an embodiment of a personal landscape view of a display of ancestral data for an individual of African-American ancestry.

FIG. 15 is a diagram illustrating an embodiment of a personal landscape view of a display of ancestral data for an individual of African-American ancestry.

In this example, there are substantial contributions to the user's ancestry from West Africa, Northern Europe, and North America. Since the locations shown in the feature correspond to the locations of the world's people (just) prior to the era of intercontinental travel, this North American ancestry refers to Native American ancestry.

In some embodiments, the personal landscape view allows users to zoom in on their results. For users with wholly European ancestry or wholly East Asian ancestry, this allows them to see their results more readily.

In various embodiments, a user interface associated with any of the displays described herein provides controls to allow the user to interact with the data.

In some embodiments, users may also switch to a discrete representation of their results by toggling a "Mosaic" option. Rather than the smoothed landscapes depicted above, the user's ancestry is represented in terms of the world's national or regional boundaries. Countries colored more darkly contribute greater proportions of the user's ancestry.

In some embodiments, this view also allows the user to specify an arbitrary subset of the genome for visualization. Thus, if a user noticed an interesting stretch on Chromosome 6 in a karyotype view, they could look at the spatial distribution of ancestry from just Chromosome 6 in their personal landscape view.

Figure 16:
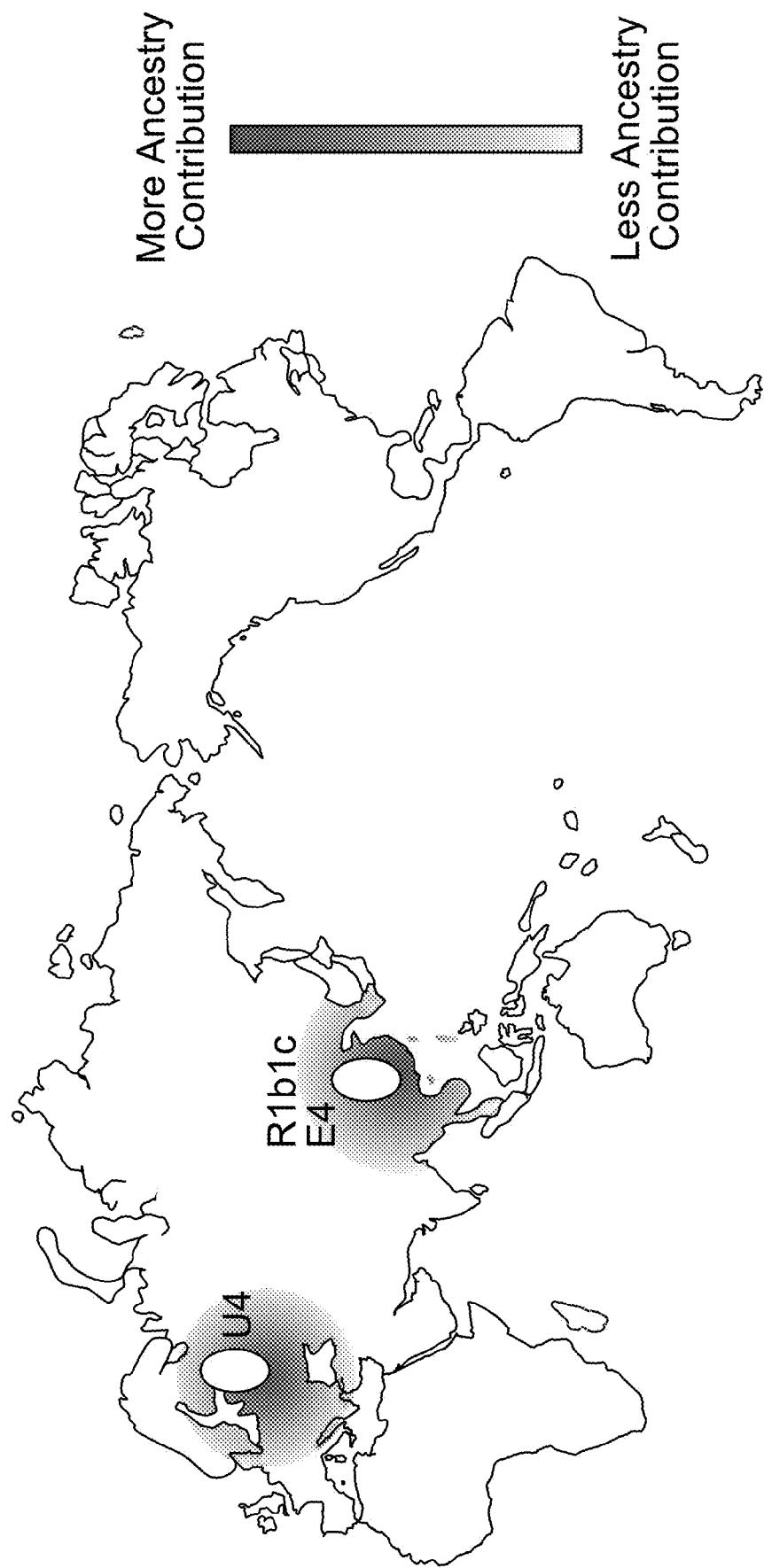
FIG. 16 is a diagram illustrating an embodiment of a personal landscape view of a display of ancestral data for an individual, in which markers are indicated.

FIG. 16 is a diagram illustrating an embodiment of a personal landscape view of a display of ancestral data for an individual, in which markers are indicated.

In some embodiments, markers can be added at the most likely geographic origins of the user's parents, grandparents, or more distant ancestors. Information can be included on each ancestor's Y and mitochondrial haplogroups, if this data is available. In this example, the user's father with Y haplogroup R1b1c, and mitochondrial haplogroup E4 is shown; the mother has mitochondrial haplogroup U4.

Figure 17:
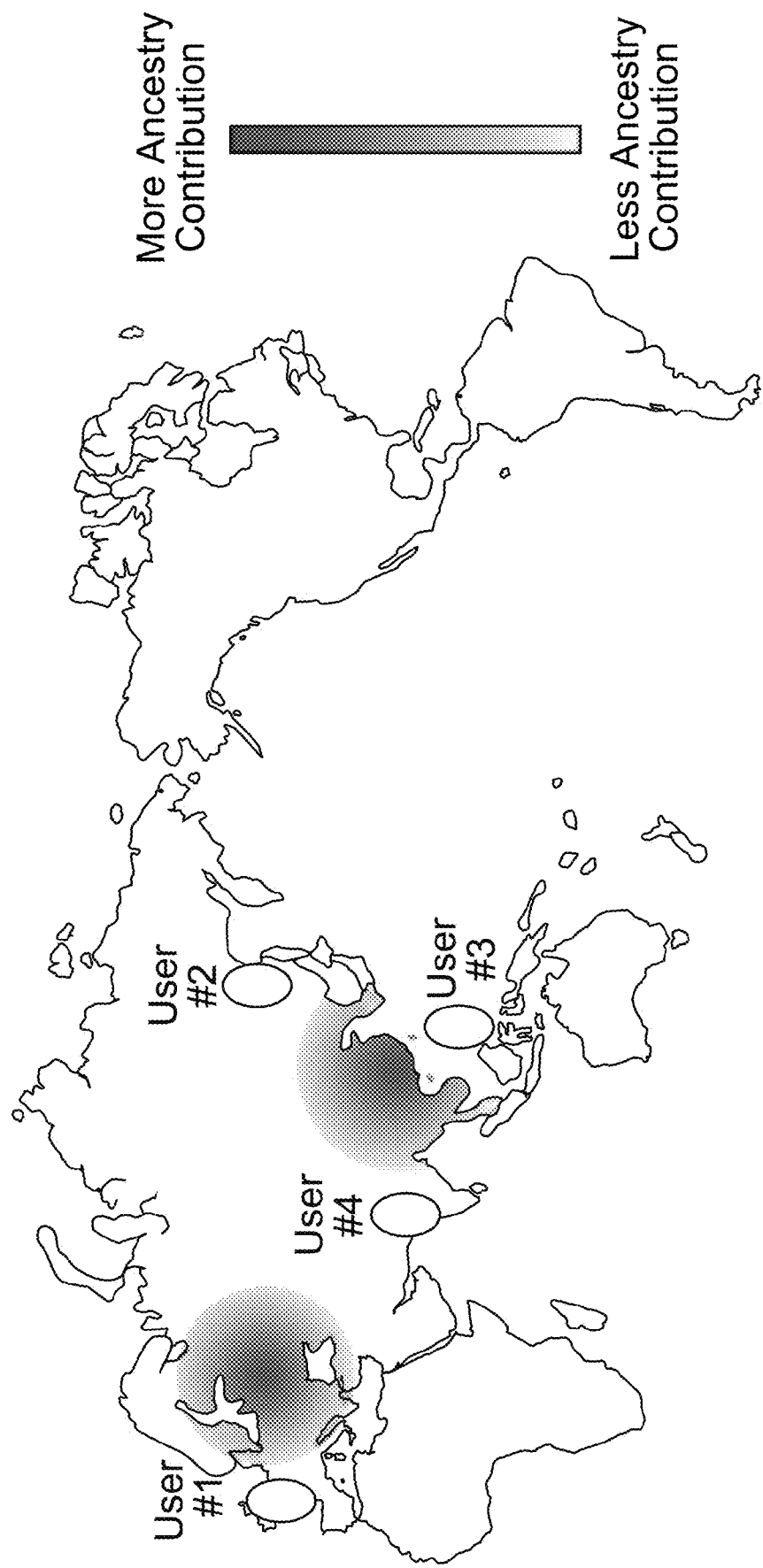
FIG. 17 is a diagram illustrating an embodiment of a personal landscape view of a display of ancestral data for an individual, in which multiple individuals are indicated.

FIG. 17 is a diagram illustrating an embodiment of a personal landscape view of a display of ancestral data for an individual, in which multiple individuals are indicated. Other individuals, such as the user's family and friends, are shown on the same map.

In some embodiments, the data may be obtained from a database associated with a website that allows individuals to view and/or share with other users their genetic data. An example of such a website is www.23andme.com. Within a database of genetic data, likely relatives can be determined by haplotype matching. In some cases, users can provide their ancestral origin; in other cases, ancestral origin can be computed using the techniques described above. These putative relatives can be displayed on the same personal landscape map. If the putative relatives appear in regions that concur with the user's own ancestry, this lends extra credence to these relationships.

Figure 18:
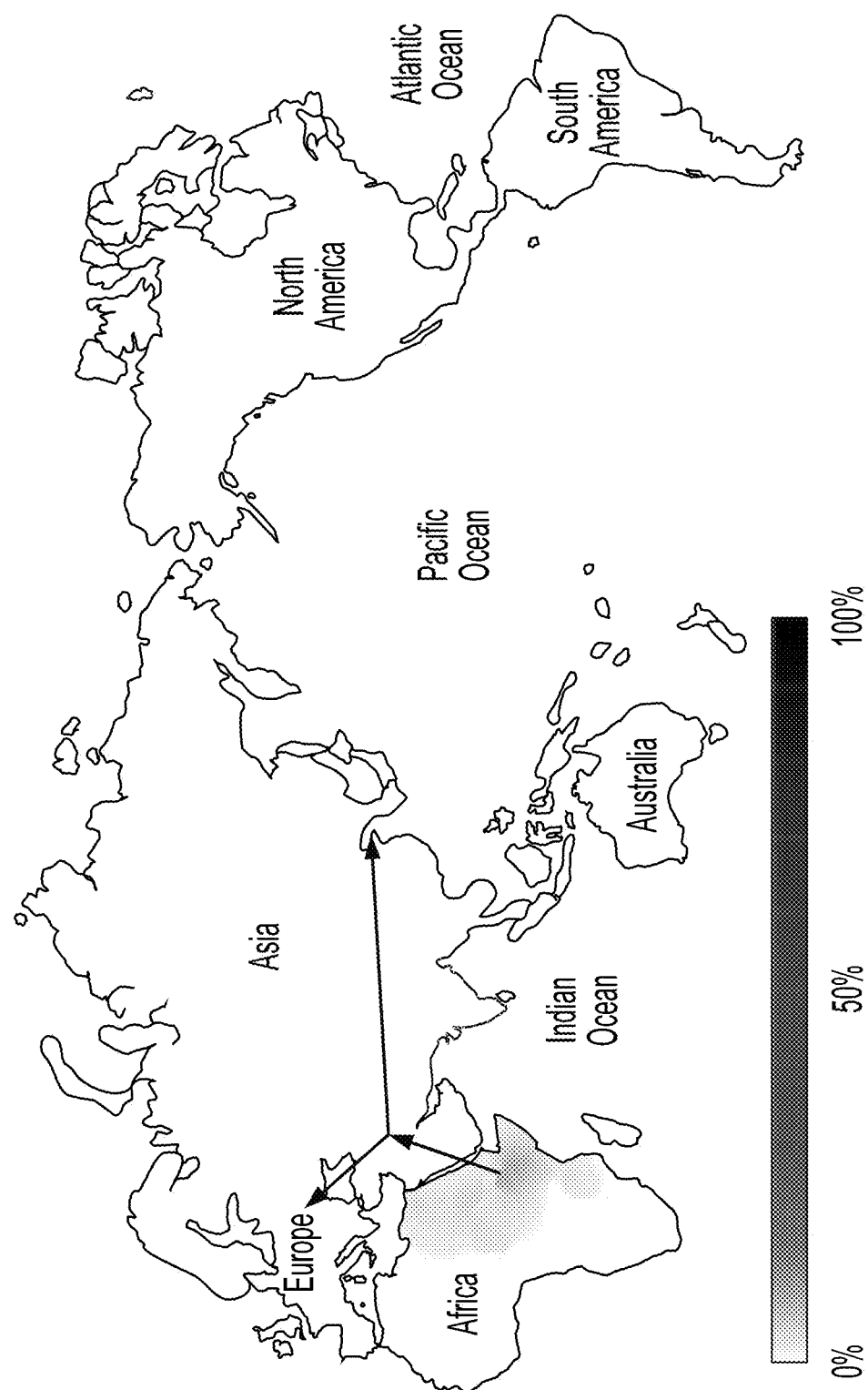
FIG. 18 is a diagram illustrating an embodiment of a personal landscape view of a display of ancestral data for an individual, in which migration information is indicated.

FIG. 18 is a diagram illustrating an embodiment of a personal landscape view of a display of ancestral data for an individual, in which migration information is indicated.

In this example, a migration of the user's ancestors is charted, by using known human migration patterns and the ultimate location of the user's haplotypes (before the era of intercontinental travel). For instance, in this example, the early migration out of Africa is shown, and from the techniques described above, it can be determined that the user's ancestors must have traveled to Asia and Europe, but not as far as the Americas.

Figure 19:
FIG. 19 is a diagram illustrating an embodiment of a tabular view of a display of ancestral data for an individual.

FIG. 19 is a diagram illustrating an embodiment of a tabular view of a display of ancestral data for an individual. This view depicts a user's ancestral origins in a readily-grasped visual three column table. It derives loosely from the treemap visualization (e.g., explained under "Treemapping" of Wikipedia).

The three divisions in the table correspond to the three levels of hierarchy in the data set: continental, regional, and local. This is a tabular view representation that might correspond to the half-European/half-Asian individual discussed above. Each of the columns in the table divide the user's ancestry into proportions (that add up to 100%). The gray-colored regions correspond to unassigned regions of the user's genome, due to noninformative markers or due to lack of data. The columns provide increased spatial resolution of assignment as they proceed to the right, and the unassignable proportion also tends to increase. Thus the assignable portion of this user's genome can be seen to be about 50/50 European/East Asian in the leftmost column. All of the European ancestry that is assignable at the regional level comes from Eastern European populations, and at the local level can be seen to be derived from Ukrainian and Russian ancestors. All of the East Asian ancestry that is assignable at the regional level comes from Eastern Chinese populations, and at the local level can be seen to be derived from Han ancestors.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A system comprising one or more processors and system memory, the one or more processors being configured to:
    receive an indication of one or more local-level origins of a complex system;
    determine one or more graphic display parameters based at least in part on the indication; and
    visually display, in an interactive graphical user interface (GUI), a graphical representation of the one or more local-level origins using the one or more graphic display parameters.

2. The system of claim 1, wherein the one or more graphic display parameters comprise a color assigned to each of the one or more local-level origins.

3. The system of claim 1, wherein the indication comprises an indication that a genetic interval of a genome of an individual corresponds to a reference interval that has a likelihood of having one or more ancestral origins.

4. A method for displaying ancestral origins, comprising:
    receiving an indication of one or more ancestral origins of a genetic interval of a genome of an individual;
    determining one or more graphic display parameters based at least in part on the indication; and
    visually displaying, in an interactive graphical user interface (GUI), a graphical representation of the one or more ancestral origins of the genetic interval using the one or more graphic display parameters.

5. The method of claim 4 wherein the one or more graphic display parameters comprise a color assigned to each of the ancestral origins of the genetic interval.

6. The method of claim 4, wherein the one or more graphic display parameters comprise a position of the genetic interval in an autosomal chromosome.

7. The method of claim 6, wherein the graphical representation of the one or more ancestral origins of the genetic interval comprises a graphical representation of the chromosome having an interval filled with a color assigned to one of the one or more ancestral origins, the interval filled with the color being at the position of the genetic interval in the autosomal chromosome.

8. The method of claim 4, wherein the one or more ancestral origins of the genetic interval are displayed using a density plot or a contour plot.

9. A computer program product for displaying ancestral origins, the computer program product being embodied in a computer readable medium and comprising computer instructions for:
    receiving an indication of one or more ancestral origins of a genetic interval of a genome of an individual;
    determining one or more graphic display parameters based at least in part on the indication; and
    visually displaying, in an interactive graphical user interface (GUI), a graphical representation of the one or more ancestral origins of the genetic interval using the one or more graphic display parameters.

10. The computer program product of claim 9, wherein the one or more graphic display parameters include a color assigned to each of the one or more ancestral origins.

11. The method of claim 4, wherein the genetic interval comprises an autosomal chromosome segment.

12. The method of claim 4, wherein the genetic interval comprises a pair of autosomal chromosome segments.

13. The method of claim 7, wherein the chromosome is divided into intervals representing a plurality of genetic intervals, including the genetic interval.

14. The method of claim 13, wherein colors are used to fill in the intervals.

15. The method of claim 4, further comprising displaying a percentage associated with each of the one or more ancestral origins.

16. The method of claim 4, wherein receiving the indication of the one or more ancestral origins of the genetic interval comprises looking up the genetic interval in a table of genotype frequencies associated with a plurality of ancestral origins to determine an ancestral assignment for the genetic interval.

17. The method of claim 4, wherein receiving the indication of the one or more ancestral origins of the genetic interval comprises using a sliding window to smooth out ancestral origin assignments.

* * * * *